United States Patent [19]
Wilson et al.

[11] Patent Number: 5,352,604
[45] Date of Patent: Oct. 4, 1994

[54] ALKALINE PROTEOLYTIC ENZYME AND METHOD OF PRODUCTION

[75] Inventors: Charles R. Wilson, Santa Rosa; Beth F. Ladin, Benicia, both of Calif.; Jonathan R. Mielenz, Littleton, Colo.; Sherman S. M. Hom, Santa Rosa, Calif.; Dieter Hansen, Langenfeld, Fed. Rep. of Germany; Robert B. Reynolds, St. Louis, Mo.; Nicholas C. T. Kennedy, Duesseldorf, Fed. Rep. of Germany; Joachim Schindler, Hilden, Fed. Rep. of Germany; Michael Bahn, Düsseldorf, Fed. Rep. of Germany; Rolf Schmid, Wolfenbuettel, Fed. Rep. of Germany; Martina Markgraf, Dusseldorf, Fed. Rep. of Germany; Christian Paech, Santa Rosa, Calif.; Karlheinz Maurer, Erkrath, Fed. Rep. of Germany

[73] Assignee: Henkel Research Corporation, Santa Rosa, Calif.

[21] Appl. No.: 33,080

[22] Filed: Mar. 10, 1993

Related U.S. Application Data

[63] Continuation of Ser. No. 398,854, Aug. 25, 1989, abandoned.

[51] Int. Cl.$^5$ .................. C12N 9/54; C12N 15/00; C12N 15/31; C12N 15/74
[52] U.S. Cl. .................. 435/221; 435/220; 435/222; 435/252.31; 435/172.3; 252/174.12; 536/23.2; 935/14; 935/27; 935/74
[58] Field of Search .................. 435/69.1, 220, 221, 435/222, 252.31, 320.1; 536/23.2

[56] References Cited

U.S. PATENT DOCUMENTS

| | | | |
|---|---|---|---|
| 4,366,246 | 12/1982 | Riggs | 435/68 |
| 4,425,437 | 1/1984 | Riggs | 435/317 |
| 4,431,739 | 2/1984 | Riggs | 435/253 |
| 4,563,424 | 1/1986 | Riggs | 435/71 |
| 4,704,362 | 11/1987 | Itakura et al. | 435/253 |
| 4,760,025 | 7/1988 | Estell et al. | 435/222 |
| 4,801,537 | 1/1989 | Nagarajan et al. | 435/68 |
| 4,914,031 | 4/1990 | Zukowski et al. | 435/222 |
| 5,116,741 | 5/1992 | Bryan et al. | 435/87 |

FOREIGN PATENT DOCUMENTS

| | | |
|---|---|---|
| 0214435 | 3/1987 | European Pat. Off. . |
| 2171703 | 9/1986 | United Kingdom . |
| 8906279 | 7/1989 | World Int. Prop. O. . |

OTHER PUBLICATIONS

Goddette, D. W. et al., 1992, Journal of Molecular Biology, 227: 001–015 (preprint of fifteen pages).
Teplyakov, A. V. et al., 1990, Journal of Molecular Biology, 214: 261–279.
Betzel, C. et al., 1990, Protein Engineering, 3(6): 161–172.
Neidhart, D. J., et al., 1988, Protein Engineering, 2(4): 271–276.
Wells, J. A. et al., 1987, Proceedings of The National Academy of Sciences, USA, 84: 1219–1223.
Russel, A. J., et al., 1987, Journal of Molecular Biology, 193: 803–813.
Chothia, C., et al., 1986, The EMBO Journal, 5(4): 823–826.

(List continued on next page.)

*Primary Examiner*—Robert A. Wax
*Assistant Examiner*—William W. Moore
*Attorney, Agent, or Firm*—Wayne C. Jaeschke; John E. Drach; Frank S. Chow

[57] ABSTRACT

A proteolytic enzyme for use in detergent formulations having increased pH and oxidative stability under typical laundering conditions in aqueous solutions is produced by fermenting *Bacillus licheniformis* host strain transformed by a multicopy plasmid comprised of DNA sequences which code for the desired proteolytic enzyme.

4 Claims, 31 Drawing Sheets

```
          5         10        15        20        25        30
          |         |         |         |         |         |
  1 M K K P L G K I V A S T A L L I S V A F S S S I A S A A E E
 31 A K E K Y L I G F N E Q E A V S E F V E Q V E A N D E V A I
 61 L S E E E E V E I E L L H E F E T I P V L S V E L S P E D V
 91 D A L E L D P A I S Y I E E D A E V T T M A Q S V P W G I S
121 R V Q A P A A H N R G L T G S G V K V A V L D T G I S T H P
151 D L N I R G G A S F V P G E P S T Q D G N G H G T H V A G T
181 I A A L N N S I G V L G V A P S A E L Y A V K V L G A D G R
211 G A I S S I A Q G L E W A G N N G M H V A N L S L G S P S P
241 S A T L E Q A V N S A T S R G V L V V A A S G N S G A S S I
271 S Y P A R Y A N A M A V G A T D Q N N N R A S F S Q Y G A G
301 L D I V A P G V N V Q S T Y P G S T Y A S L N G T S H A T P
331 H V A G A A A L V K Q K N P S W S N V Q I R N H L K N T A T
361 S L G S T N L Y G S G L V N A E A A T R
```

Amino acid composition
-----------------------

| | | | | |
|---|---|---|---|---|
| 54 A | 0 C | 8 H | 5 M | 21 T |
| 9 R | 12 Q | 19 I | 6 F | 3 W |
| 24 N | 28 E | 30 L | 17 P | 9 Y |
| 11 D | 36 G | 10 K | 43 S | 36 V |

Number of residues: 380
Molecular weight (MW): 38951

OTHER PUBLICATIONS

Estell, D. A., et al., 1986, Science, 233: 659–663.
Carter, P. and Wells, J. A., 1987, Protein Engineering 1: 234 (note 29).
Aewick, R. M., et al., 1981, The Journal of Biological Chemistry 256(15): 7990–7997.
*A–GreSeq*–4 database search, FIG. 29, Nov. 14, 1991.
*PIR*14 29 database search, FIG. 29 sequence, Nov. 14, 1991.
*Swiss Prot*–19 database search FIG. 29 sequence, Nov. 14, 1991.
Betzel, C., et al., 1988, Journal of Molecular Biolgoy, 204: 803–804.
Gordon, R. E., et al., 1982, Journal of General Microbiology 128: 1109–1116.
Meloun, B., et al., 1985, FEBS Letters, 183(2): 195–199.
Owens–Narhi, L., et al., 1988, Archives of Biochemistry and Biophysics, 261(1): 161–169.

```
              5         10        15        20        25        30
              |         |         |         |         |         |
  1 M K K P L G K I V A S T A L L I S V A F S S S I A S A A E E
 31 A K E K Y L I G F N E Q E A V S E F V E Q V E A N D E V A I
 61 L S E E E E V E I E L L H E F E T I P V L S V E L S P E D V
 91 D A L E L D P A I S Y I E E D A E V T T M A Q S V P W G I S
121 R V Q A P A A H N R G L T G S G V K V A V L D T G I S T H P
151 D L N I R G G A S F V P G E P S T Q D G N H G T H V A G T
181 I A A L N N S I G V L G V A P S A E L Y A V K V L G A D G R
211 G A I S S I A Q G L E W A G N N G M H V A N L S L G S P S P
241 S A T L E Q A V N S A T S R G V L V V A A S G N S G A S S I
271 S Y P A R Y A N A M A V G A T D Q N N R A S F S Q Y G A G
301 L D I V A P G V N V Q S T Y P G S T Y A S L N G T S M A T P
331 H V A G A A A L V K Q K N P S W S N V Q I R N H L K N T A T
361 S L G S T N L Y G S G L V N A E A A T R
```

Amino acid composition
----------------------

| 54 A | 0 C  | 8 H  | 5 M  | 21 T |
| 9 R  | 12 Q | 19 I | 6 F  | 3 W  |
| 24 N | 28 E | 30 L | 17 P | 9 Y  |
| 11 D | 36 G | 10 K | 43 S | 36 V |

Number of residues: 380
Molecular weight (MW): 38951

```
              10        20        30        40        50
              |         |         |         |         |
   1 AAGCTTCTAGAGATCTTCCATACCTACCAGTTCTGCGCCTGCAGCAATGG
  51 CAACAACGTCGCGGATCATTACAAAGACGATTGCCAAGGCCGCTAACTGA
 101 ATACTGCTAGCTGTGTACCACTGTAAAGCGAAAGGTGCGTCTAAGTAATA
 151 AGGCCGAACCTTAAATTAAATTCCCTCGTTTGCCCACACAGGCTTTTTAG
 201 GCGTGTGTATTTTGTTATGCCTAGTAGAATCAAAATAGACATAAGAACTG
 251 GAGGACTTATTATATGCATGAACAATTGAGACAAACGACACAACCAACGA
 301 TTATTGTTGGTGTGGAGTTCGAAAAAGACACGGATTTCCACTATTCGATG
 351 GAAGAATTGAACAATTTGGCCGATCGCTTGATTTGCAGGTTGTCGACAGC
 401 TCACACAAAAGCTGCCTGTACCAAATCAAGCGACATATATTGGTGCTGGC
 451 AAAGCGTCTGAGCTTTCCTGATGTGTGAATCGCTTGGGGGCTACGCTCGT
 501 TGTGTTTAATGACGAGCTCTCACCTTCACAAATCCGCAATCTTGAAAAAT
 551 TGCTGGAAGTAACCGTTTATGATCGGACCATGTTGATTTTAGATATTTTT
 601 GGCGAAAGGGCGAAGACGAAAGAAGCTCAACTCCAAGTAGAAATGGCGCG
 651 CTGCCGCTATTTGTTCGCACGGCTCGTCGGCATGCGCGCTTCATTAAGCA
 701 GGCAAGGCGGCCGGCACTGGCTTGGCCAACCGCGGCGCCGGGGAAACAAA
 751 GTTGGAGCTCGATCGTCGTAAAATTGAAACACGTATTCATGCGTTGGAAA
 801 AAGAGCTGGAAGACGTTGTCAAACGACGCGAGTTACAGCGCAAACGCCGG
 851 AAAAAACAAGCGATGCCGGTCGTTGCCTTAGTTGGCTATACAAATGCAGG
 901 GAAATCTTCGCTGCTGAATGCGCTGTTGGACGATGCCGAGGAAAAGCGTG
 951 TGTTGGAAAAGATATGTTGTTTGCCACTCTTGATACGTCTGTGCGTAAA
1001 GTGGAACTTGACAAAAACCATTCTGTTTTATTAGCGGATACGGTTGGCTT
1051 TGTCTCTAAATTGCCAACACACCTCGTTAAAGCATTCCGCTCAACATTGG
1101 AAGAAGCTCGGGAAGCCGATTTGCTACTGCATGTCGTCGATTATTCAAAT
1151 GAACGCCATCGCGAAATGGCAAAGACGACAAATGAAACACTCCAGGCAAT
1201 GGAAATCGATCGCCCGATGATTTATGTTTACAACAAAATGGATCGAGTGA
1251 AAGACGCGTTTCCTCAAGCGCATGGGCACGAGCTGTTTATATCAGCTAAG
1301 GCTAAACAAGGGCTTGATTTATTAGCACAGAAAATAGCAAGCTATGTTTT
1351 TCAAGATTTTGAAAAACATCTGTTCATCATTCCTTATCGTGACGGGGAGG
1401 CGGCTGCTTATTTAAACAACCATGCCCATGTTCACACACAGCGTGCTGAG
1451 GAGGACGGCTGGCATATCGTTGCCGATTTGCATGAACGAGACTTGAAACG
1501 GGTTGAAAGCTACTGTGTTTCAAAAGAACGATAATGAAAAAAGCCATTTG
1551 AATGCTTCTTGTTCAAATGGCTTTTTGGCGACTATGGTAGACAGATGAAC
1601 ACTTGTTTCGCTGTTTTACGACAAAGATCATCCTGCCTGTTACGCGTTTT
1651 TTAAATCCGTTTTCGCACGTTCAATTGTCGCCGAGTCGTACCAGTCGCTG
1701 TAAGTGAGAATATGTTTAGAAAGCCGCGTATTTAAGCGCAGTCTTTTTCG
1751 TTCTGTACTGGCTGGTTTGTGGACAGTTTCCATACCCATCGGCCTCCTTT
1801 TATTTGTAGCTTTCCCCACTTGAAACCGTTTTAATCAAAAAAGAAACGGG
1851 AAGATTCTGTTAACTTAACGTTAATATTTGTTTCCCAATAGGCAAATCTT
1901 TCTAACTTTGATACGTTTAAACTACCAGCTTGGACAAGTTGGTATAAAAA
1951 TGAGGAGGGAACCGAATGAAGAAACCGTTGGGGAAAATTGTCGCAAGCAC
2001 CGCACTACTCATTTCTGTTGCTTTTAGTTCATGCATCGCATCGGCTGCTG
2051 AGGAAGCAAAAGAAAAATATTTAATTGGCTTTAATGAGCAGGAAGCTGTC
2101 AGTGAGTTTGTAGAACAAGTAGAGGCAAATGACGAGGTCGCCATTCTCTC
2151 TGAGGAAGAGGAAGTCGAAATTGAATTGCTTCATGAGTTTGAAACGATTC
2201 CTGTTTTATCCGTTGAGTTAAGCCCAGAAGATGTGGACGCGCTTGAACTT
2251 GATCCAGCGATTTCTTATATTGAAGAGGATGCAGAAGTAACGACAATGGC
2301 GCAATCAGTGCCATGGGGAATTAGCCGTGTGCAAGCCCCGGCTGCCCATA
2351 ACCGTGGATTGACAGGTTCTGGTGTAAAAGTTGCTGTCCTCGATACAGGT
```

```
2401 ATTTCCACTCATCCAGACTTAAATATTCGTGGTGGCGCTAGCTTTGTACC
2451 AGGGGAACCATCCACTCAAGATGGGAATGGGCATGGCACGCATGTGGCCG
2501 GGACGATTGCTGCTTTAAACAATTCGATTGGCGTTCTTGGCGTAGCGCCT
2551 AGTGCGGAACTATACGCTGTTAAAGTTTTAGGAGCCGACGGTAGAGGTGC
2601 AATCAGCTCGATTGCCCAAGGGTTGGAATGGGCAGGGAACAATGGCATGC
2651 ACGTTGCTAATTTGAGTTTAGGAAGCCCTTCGCCAAGTGCCACACTTGAG
2701 CAAGCTGTTAATAGCGCGACTTCTAGAGGCGTTCTTGTTGTAGCGGCATC
2751 TGGGAATTCAGGTGCAAGCTCAATCAGCTATCCGGCCCGTTATGCGAACG
2801 CAATGGCAGTCGGAGCTACTGACCAAAACAACAACCGCGCCAGCTTTTCA
2851 CAGTATGGCGCAGGGCTTGACATTGTCGCACCAGGGGTAAACGTGCAGAG
2901 CACATACCCAGGTTCAACGTATGCCAGCTTAAACGGTACATCGATGGCTA
2951 CACCTCATGTTGCAGGTGCAGCAGCCCTTGTTAAACAAAAGAACCCATCT
3001 TGGTCCAATGTACAAATCCGCAACCATCTAAAGAATACGGCAACGAGCTT
3051 AGGAAGCACGAACTTGTATGGAAGCGGACTTGTCAATGCAGAAGCGGCAA
3101 CACGCTAATCAATAAAAAAACCGTGTGCGCTTAAAGGGCACAGCTTTTTT
3151 TGTGTATGAATCGAAAAAAGAGAACAGATCGCAGGTCTCAAAAATCGAGC
3201 GTAAAGGGTTGTTTAAAGCTCTTTACGCTCGCAGGTCTTATCGCTATACA
3251 ATGGAAAATTCACGTCTTTTGACTTTCATGGCATATATTTATTTAAGTAT
3301 TCGTTTGCTTTTTCGTACTCTCCGTTTTTCTGGTACCATTGCGCCAGCTC
3351 AATTGCATAGTGGACTGGTTCTTCTTTATTATCAAGCTT
```

Total number of bases is: 3389,
DNA sequence composition: 949 A; 716 C; 820 G; 904 T;

FIG. 2-2

```
              80                    100
#1  5' - GGCCCTCGGGACCTCTTTCCC - 3'   (53926, top strand)
            Ava I 651                   633
2  5' - GGAATGCCccAtGGAACGG - 3'   (53926, bottom strand)
               Nco I 390                         361
3  5' - GCGGAATCGaTcgATGCCATCGTGAACACG - 3'   (53926, bottom strand)
               Cla I
```

```
N02.1    5'   GGCAGATCTGTXCCXTGGGGGAT-3'
N02.2    5'   GGCAGATCTGTXCCXTGGGGAAT-3'
N02.3    5'   GGCAGATCTGTXCCXTGGGGTAT-3'
N02.4    5'   GGCAGATCTGTXCCXTGGGGCAT-3'

A  T       T
N04.1    5'   GTCCCGTGGGGXATCAG-3'
                               A
                     G  T       T
N04.2    5'   GTTCCGTGGGGXATCAG-3'
                               A
                     A  T       T
N04.3    5'   GTCCCGTGGGGXATCTC-3'
                               A
                     G  T       T
N04.4    5'   GTTCCGTGGGGXATCTC-3'
                               A

A  A  A  A    T
C03.1    5'   CCCGCCACGTGCGGCGT-3'

G  G  A  A    T
C03.2    5'   CCTGCTACGTGCGGCGT-3'

G  A  A  A    T
C03.3    5'   CCTGCCACGTGCGGCGT-3'

A  G  A  A    T
C03.4    5'   CCCGCTACGTGCGGCGT-3'
```

X = (A,T,G or C)

FIG. 26
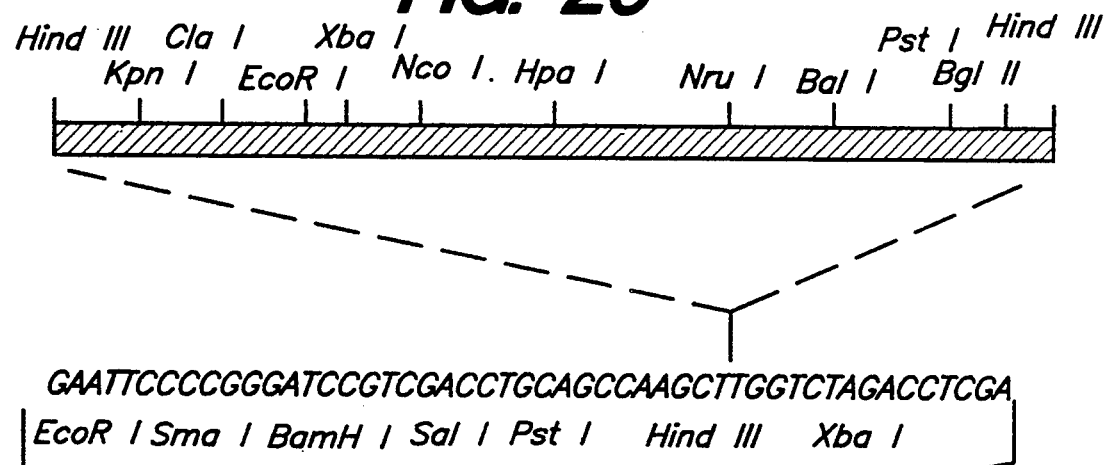
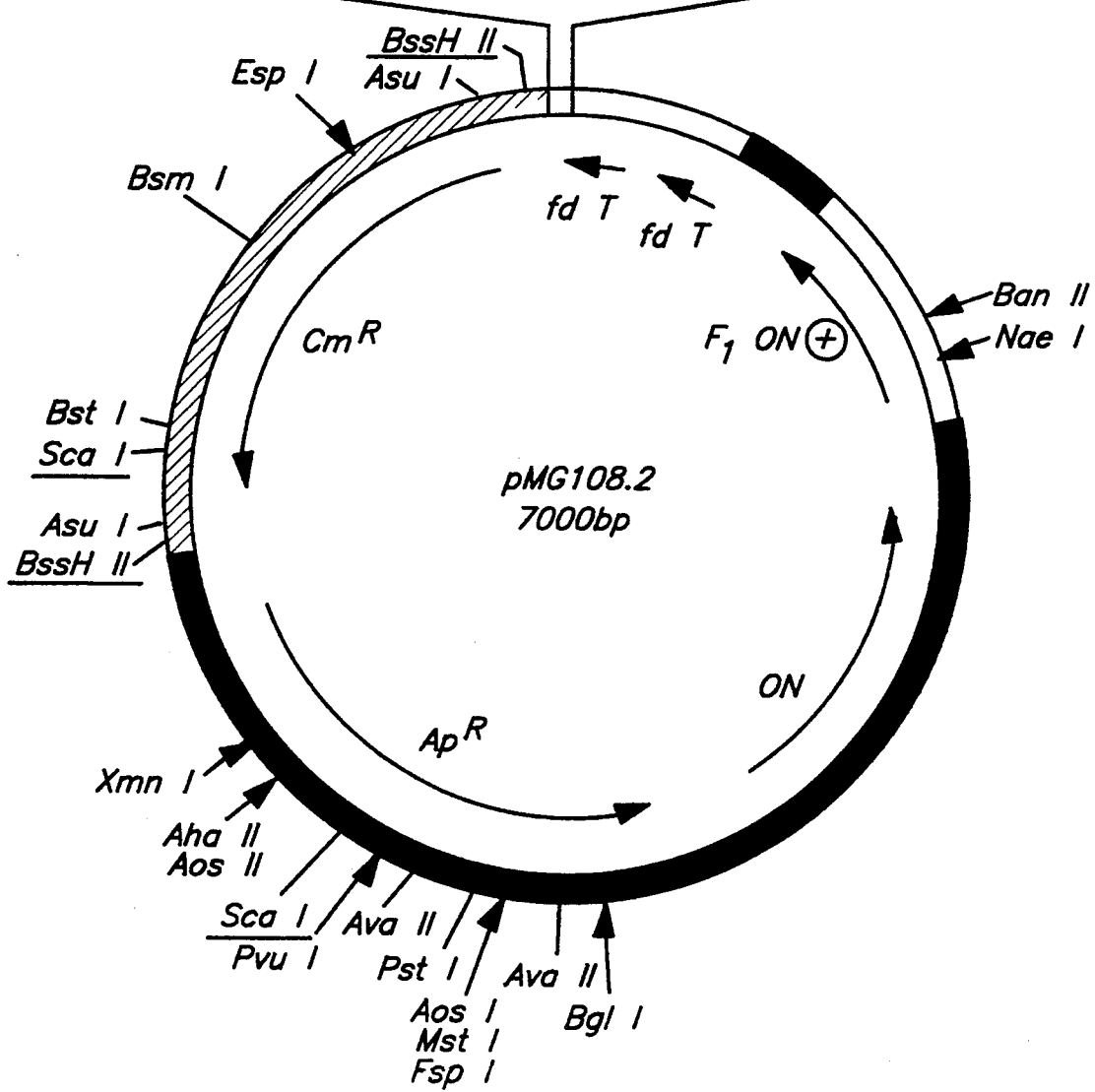

FIG. 27

```
              10        20        30        40        50
              |         |         |         |         |
  1  GTCTCCTGGATCTCATAAAATAAATGAATAGTATTTTCATAAAATGAATC

51  ATATGGATGCAATCTCCTGTCATTCTGCTGGCCCTCGGGACCTCTTTCCC

101  TCGGAGGCTGAAGCGGTCTATTCATACTTTCGAACTGAACATTTTTCTAA

151  AACAGTTATTAATAACCAAAAAATTTTAAATTGGTCCTCCAAAAAAATAG
                                         TRANSCRIPTION START SITE
201  GCCTACCATATAATTCATTTTTTTTCTATAATAAATTAACAGAATAATTG

251  GAATAGATTATATTATCCTTCTATTTAAATTATTCTGAATAAAGAGGAGG
                   PRE-SEQUENCE
301  AGAGTGAGTAATGATGAGGAAAAAGAGTTTTTGGCTTGGGATGCTGACGG
                      CG  T                      PRO SEQUENCE
351  CCTTCATGCTCGTGTTCACGATGGCATTCAGCGATTCCGCTTCTGCTGCT
                              Cla I
401  CAACCGGCGAAAAATGTTGAAAAGGATTATATTGTCGGATTTAAGTCAGG

451  AGTGAAAACCGCATCTGTCAAAAAGGACATCATCAAAGAGAGCGGCGGAA

501  AAGTGGACAAGCAGTTTAGAATCATCAACGCGGCAAAAGCGAAGCTAGAC

551  AAAGAAGCGCTTAAGGAAGTCAAAAATGATCCGGATGTCGCTTATGTGGA
                                   MATURE PROTEASE
                                          A  GG
601  AGAGGATCATGTGGCCCATGCCTTGGCGCAAACCGTTCCTTACGGCATTC
                                      Nco I
651  CTCTCATTAAAGCGGACAAAGTGCAGGCTCAAGGCTTTAAGGGAGCGAAT

701  GTAAAAGTAGCCGTCCTGGATACAGGAATCCAAGCTTCTCATCCGGACTT

751  GAACGTAGTCGGCGGAGCAAGCTTTGTGGCTGGCGAAGCTTATAACACCG
```

801 ACGGCAACGGACACGGCACACATGTTGCCGGTACAGTAGCTGCGCTTGAC

851 AATACAACGGGTGTATTAGGCGTTGCGCCAAGCGTATCCTTGTACGCGGT

901 TAAAGTACTGAATTCAAGCGGAAGCGGATCATACAGCGGCATTGTAAGCG
          T C
951 GAATCGAGTGGGCGACAACAAACGGCATGGATGTTATCAATATGAGCCTT
    Kpn I
1001 GGGGGAGCATCAGGCTCGACAGCGATGAAACAGGCAGTCGACAATGCATA

1051 TGCAAGAGGGGTTGTCGTTGTAGCTGCAGCAGGGAACAGCGGATCTTCAG

1101 GAAACACGAATACAATTGGCTATCCTGCAAAATACGATTCTGTCATCGCT

1151 GTTGGTGCGGTAGACTCTAACAGCAACAGAGCTTCATTTTCCAGCGTCGG

1201 AGCAGAGCTTGAAGTCATGGCTCCTGGCGCAGGCGTATACAGCACTTACC

1251 CAACGAACACTTATGCAACATTGAACGGAACGTCAATGGCTTCTCCTCAT

1301 GTAGCGGGAGCAGCAGCTTTGATCTTGTCAAAACATCCGAACCTTTCAGC
                                                  T C
1351 TTCACAAGTCCGCAACCGTCTCTCCAGCACGGCGACTTATTTGGGAAGCT
                                               Kpn I
1401 CCTTCTACTATGGGAAAGGTCTGATCAATGTCGAAGCTGCCGCTCAATAA

1451 CATATTCTAACAAATAGCATATAGAAAAAGCTAGTGTTTTTAGCACTAGC

1501 TTTTTCTTCATTCTGATGAAGGTTGTTCAATATTTTGAATCCGTTCCATG
              G AC
1551 ATCGTCGGATGGCCGTATTTAAAAATCTTGACGAGAAACGGCGGGTTTGC
         Kpn I
1601 CTCGCTCAGCCCGGCTTTTGAGAGCTCTTGAAACGTCGAAACCGCTGCAT

1651 CGCTGTTTTGCGTCAGTTCAATCGCATACTGGTCAGCAGCTTTTCCTGAT

1701 GCCTGAAACTGCTGCTAAATGAGACGA

FIG. 27A

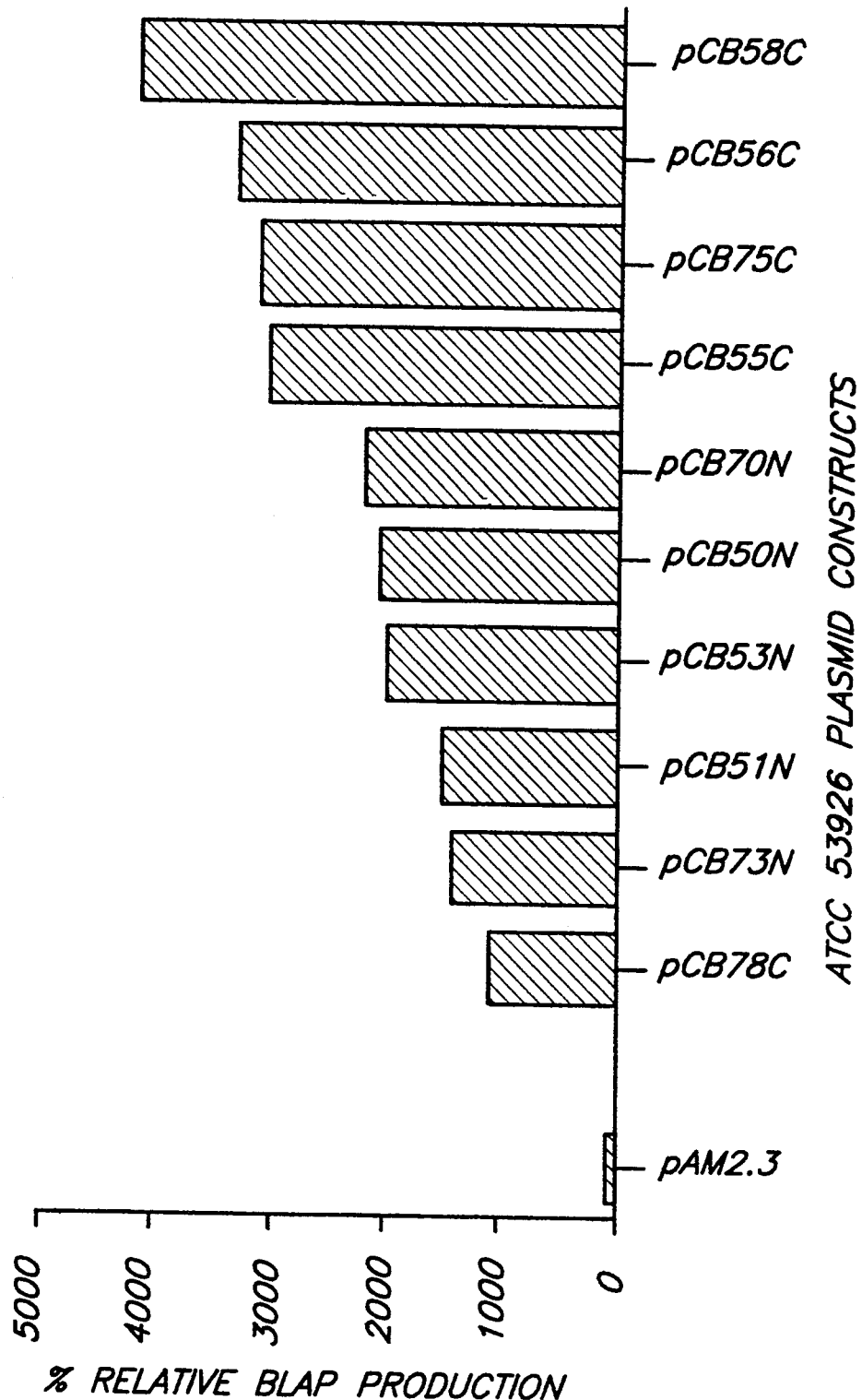

```
              5          10         15         20         25         30
              |          |          |          |          |          |
  1   A Q T V P W G I S R V Q A P A A H N R G L T G S G V K V A V
 31   L D T G I S T H P D L N I R G G A S F V P G E P S T Q D G N
 61   G H G T H V A G T I A A L N N S I G V L G V A P S A E L Y A
 91   V K V L G A D G R G A I S S I A Q G L E W A G N N G M H V A
121   N L S L G S P S P S A T L E Q A V N S A T S R G V L V V A A
151   S G N S G A S S I S Y P A R Y A N A M A V G A T D Q N N N R
181   A S F S Q Y G A G L D I V A P G V N V Q S T Y P G S T Y A S
211   L N G T S M A T P H V A G A A A L V K Q K N P S W S N V Q I
241   R N H L K N T A T S L G S T N L Y G S G L V N A E A A T R
```

Amino acid composition
----------------------

| 41 A | 0 C  | 7 H  | 3 M  | 18 T |
| 9 R  | 10 Q | 10 I | 2 F  | 3 W  |
| 22 N | 5 E  | 19 L | 13 P | 7 Y  |
| 6 D  | 34 G | 5 K  | 31 S | 24 V |

Number of residues: 269
Molecular weight (MW): 26837

*FIG. 29*

ALKALINE PROTEOLYTIC ENZYME AND METHOD OF PRODUCTION

This application is a continuation of application Ser. No. 07/398,854 filed on Aug. 25, 1989, now abandoned.

BACKGROUND OF THE INVENTION

1. Field of the Invention

This invention relates to an alkaline proteolytic enzyme, its production by cultivating genetically modified Bacillus strains, and the genetic constructs within the Bacillus strains which code for the alkaline proteolytic enzyme.

2. Description of the Related Art

Proteolytic enzymes are widely used in household laundry detergent formulations to remove protein-based stains from articles of clothing and the like. These enzymes are members of the class known as serine proteases, enzymes which catalyze the cleavage of peptide bonds. To be useful in aqueous detergent solutions, these enzymes must be active at pH values ranging from 7 to 10. They must also be stable to oxidation and enzymatic and non-enzymatic hydrolysis in order to be useful in detergent applications. Various Bacillus strains produce serine proteases under suitable aerobic fermentation conditions. However, the amount of protease made by the wild-type strains and the rate of production of the protease is usually insufficient for commercial production. One method of increasing the protease yield is to generate mutant strains through exposure to radiation or chemical mutagens. However, these classical mutation processes suffer from the disadvantage that they produce only a statistical distribution of the desired mutation and/or that a significant population reverts back to the wild type. In recent years, efforts to overcome these problems have centered on directed genetic modification of bacterial strains. This is accomplished through the introduction of recombinant DNA into host cells under circumstances guaranteeing that the host cells will replicate the recombinant DNA with an increased copy number. In addition, the genes carried by the foreign DNA must be able to be expressed. The genetically engineered organisms do not suffer from the disadvantages often exhibited by classically mutagenized bacteria and are, therefore, often useful for commercial enzyme production.

Methods of making proteases using recombinant DNA technology are known. For example, European Patent EP130756A discloses a method for preparing carbonyl hydrolase (a protease), U.S. Pat. No. 4,760,025 discloses a subtilisin from having an altered amino acid sequence than that produced by the naturally occuring strain. German patent No. DE 2925427 discloses a Bacillus alkaline protease which is highly stable to chelating agents and surfactants, and is produced by fermentation of a *Bacillus licheniformis* strain. Production of an alkaline proteolytic enzyme by cultivation of *B. licheniformis* has been described in British patent No. 1,263,765; German patent No. 1,940,488; Russian patent No. 400,116; U.S. Pat. Nos. 3,623,956; 3,623,957.

SUMMARY OF THE INVENTION

It is an object of the present invention to provide a proteolytic enzyme for use in detergent formulations having increased protease and oxidative stability under conditions of pH 7-10 and at temperatures of 10°-60° C. in aqueous solutions. It is also an object of the present invention to provide mutant Bacillus strains for use in the commercial production of proteolytic enzymes useful in detergent formulations. It is a further object of the present invention to provide expression vectors containing sequences which encode the desired proteolytic enzyme for transforming host Bacillus cells. These objectives are accomplished by providing a mature proteolytic enzyme having the amino acid sequence substantially as shown in FIG. 1. The mature proteolytic enzyme has the amino acid sequence which extends from about amino acid residue number 112 to about amino acid residue number 380. This proteolytic enzyme is obtained by cultivating a *B. licheniformis* ATCC 53926 strain which has been transformed by a plasmid having a DNA sequence comprising in the direction of transcription a regulatory region, said regulatory region comprising in the order of transcription a *B. licheniformis* ATCC 53926 alkaline protease gene promoter, ribosome binding site, and initiation codon operably linked to a pre-pro region, said pre-pro region operably linked to a mature region encoding for the *Bacillus lentus* alkaline protease enzyme.

The strain *Bacillus licheniformis* ATCC 53926 will hereinafter be referred to as ATCC 53926. The strain *Bacillus licheniformis* DSM 641 will hereinafter be referred to as DSM 641. The Polymerase Chain Reaction which is described in U.S. Pat. Nos. 4,683,195 and 4,683,202 will hereinafter be referred to as PCR. The *Bacillus licheniformis* ATCC 53926 alkaline protease gene, shown in FIG. 27, will hereinafter be referred to as ATCC 53926 alkaline protease gene. *Bacillus lentus* alkaline protease will hereinafter be referred to as BLAP. The *Bacillus licheniformis* ATCC 53926 alkaline protease gene promoter is the promoter from the ATCC 53926 alkaline protease gene and will hereinafter be referred to as the ATCC 53926 alkaline protease gene promoter. The abbreviation kb will hereinafter be used in place of 1,000 base pairs.

BRIEF DESCRIPTION OF THE FIGURES

FIG. 1 shows the amino acid sequence for the pre, pro, and mature regions of the BLAP protein.

FIG. 2 shows the DNA sequence for the 3.4 kb HindIII fragment from *Bacillus lentus* which includes the BLAP gene.

FIG. 8 shows the oligonucleotides 1-3. Positions correspond to the positions of the nucleotide sequences within the ATCC 53926 alkaline protease gene. Mismatch positions are indicated by the use of lower case letters. Restriction sites are underlined and indicated.

FIG. 25 shows the specific sequence of oligonucleotide probes and primers.

FIG. 26 shows the restriction map for plasmid pMG108.2

FIGS. 27 and 27a show the introduction of restriction sites into the gene encoding the ATCC 53926 alkaline protease gene.

FIG. 28 shows a comparison of the relative protease yields of the different ATCC 53926 alkaline protease-BLAP constructs in the ATCC 53926 production strain.

FIG. 29 shows the amino acid sequence of the mature protease made from the ATCC 53926 alkaline protease-BLAP NcoI gene fusion constructs.

DESCRIPTION OF THE PREFERRED EMBODIMENTS

Figure 3:
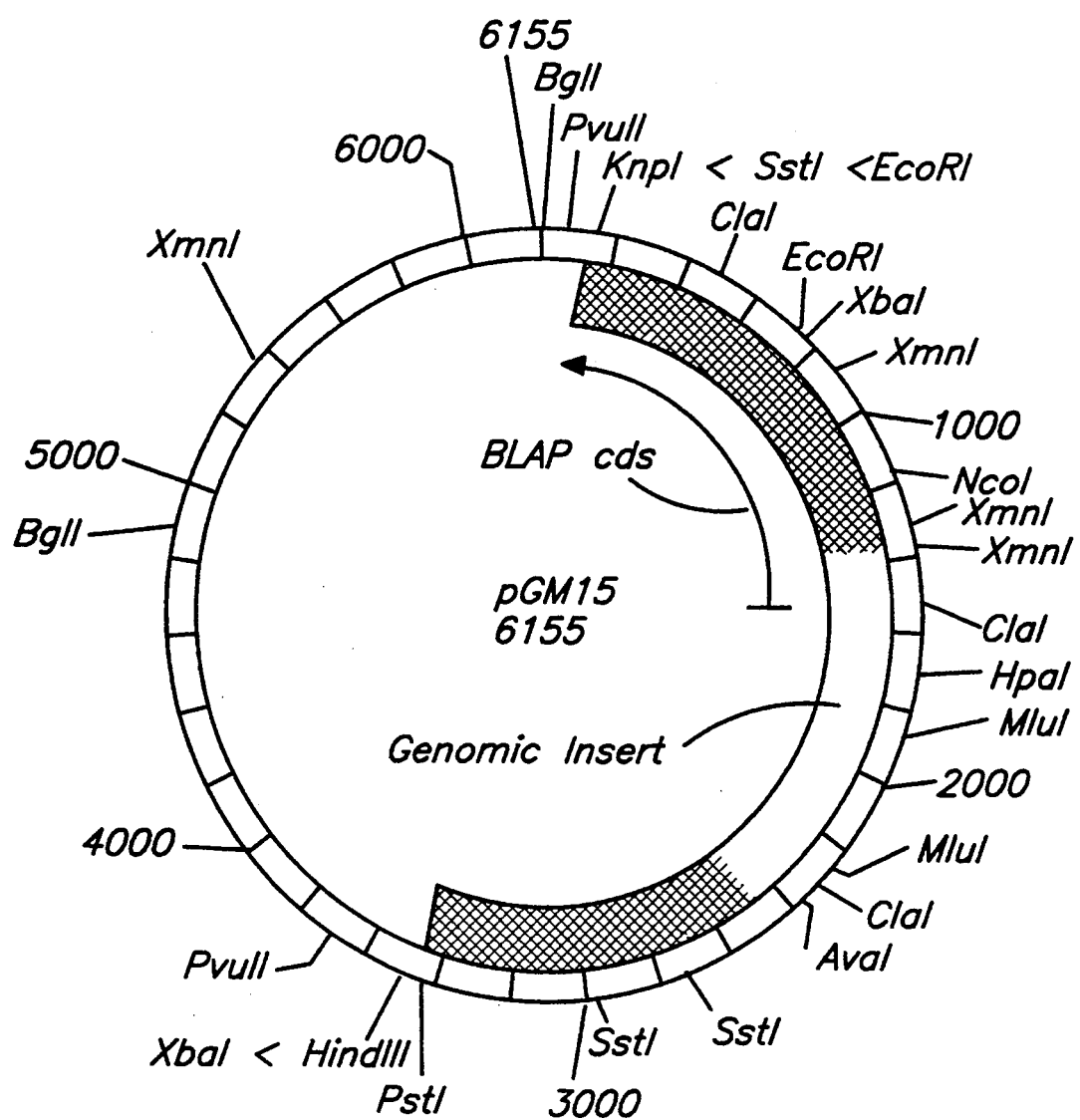
FIG. 3 shows the restriction map of plasmid pGM15.

A proteolytic enzyme (BLAP) produced by *B. lentus*, is provided having increased protease and oxidative stability in aqueous solutions of pH 7–10 and at temperatures of from 10°–60° C. The mature BLAP enzyme is a polypeptide having 269 amino acid residues, a molecular weight of 26,823 daltons, and a calculated isoelectric point of 9.7. It was first obtained from *B. lentus* DSM 5483, an organism isolated from soil samples and having the properties listed in Table I.

TABLE I

Properties of *B. lentus* DSM 5483

| | |
|---|---|
| TAXONOMIC NAME | *B. lentus* (Group II) |
| MORPHOLOGY | Vegetative Cells: |
| | Rods |
| | Width 0.6–0.8 m |
| | Length 1.5–3.5 m |
| | Spores: |
| | Ellipsoid |
| | Sporangium not swollen |
| MOBILITY | Motile |
| GRAM REACTION | Positive |
| CATALASE | Positive |
| ANAEROBIC GROWTH | Negative |
| VOGUES-PROSKAUER REACTION | Negative |
| | pH in Vogues-Proskauer medium: 6.2 |
| GROWTH PARAMETERS | TEMPERATURE |

TABLE I-continued

Properties of *B. lentus* DSM 5483

| | | |
|---|---|---|
| | Growth | 50° C. |
| | No growth | 55° C. |
| | Optimal | 39° C. |
| | pH: | |
| | Growth | pH 7.5–pH 9.5 |
| | No growth | pH 5.7 |
| | SALT TOLERANCE | |
| | Grows in 5% NaCl | |
| | Grows in 7% NaCl | |
| | Grows in 10% NaCl | |
| | SUITABLE MEDIUM: | |
| | Potato Starch | 10 g/l |
| | Yeast Extract | 10 g/l |
| | Peptone | 5 g/l |
| | $Na_2S_2O_3 \cdot 5H_2O$ | 2.5 g/l |
| | $K_2HPO_4$ | 2 g/l |
| | $Na_2MoO_4 \cdot 2H_2O$ | 1.2 g/l |
| | $NH_4Cl$ | 1 g/l |
| | $FeCl_3 \cdot 6H_2O$ | 540 mg/l |
| | MgO | 500 mg/l |
| | $CaCO_3$ | 200 mg/l |
| | $MnCl_2 \cdot 4H_2O$ | 100 mg/l |
| | ZnO | 40 mg/l |
| | $CoCl_2 \cdot 6H_2O$ | 24 mg/l |
| | $CuCl_2 \cdot 2H_2O$ | 20 mg/l |
| | $H_3BO_4$ | 3 mg/l |
| ACID PRODUCTION FROM: | Glucose | (weak) |
| | L-Arabanose | (weak) |
| | Xylose | (weak) |
| | Mannitol | (weak) |
| GAS PRODUCTION FROM GLUCOSE | Negative | |
| LECITHINASE | Negative | |
| HYDROLYSIS | Starch: | Positive |
| | Gelatin: | Positive |
| | Casein: | Positive |
| ACID UTILIZATION | Citrate: | Positive |
| | Propionate: | Negative |
| TYROSINE DEGRADATION | Negative | |
| INDOLE REACTION | Negative | |
| PHENYLALANINE DEAMINASE | Negative | |
| ARGININE DEHYDROLASE | Negative | |
| NITRATE REDUCTION | Nitrate reduced to nitrite | |

The amino acid sequence, shown in FIG. 1 was determined in part by standard amino acid sequencing techniques, and the rest deduced from the nucleic acid sequence.

A method is presented for producing the BLAP enzyme comprising cultivating a Bacillus host cell containing a hybrid plasmid having a DNA sequence coding for the BLAP enzyme comprising in the direction of transcription, a regulatory region, said regulatory region comprising in the order of transcription a ATCC 53926 alkaline protease gene promoter, ribosome binding site, and initiation codon operably linked to a pre-pro region, said pre-pro region operably linked to a mature region encoding for the BLAP enzyme. All the above may be linked to a carboxy terminal (C-terminal) DNA sequence from ATCC 53926 alkaline protease gene. The C-terminal DNA sequence is a DNA sequence between approximately the SalI and approximately the SstI restriction sites of the ATCC 53926 alkaline protease gene. It may be used to suppress chromosomally encoded protease as disclosed in a copending U.S. patent application. Any Bacillus strain can be used in the method of the present invention to produce the BLAP enzyme. *B. licheniformis* is the preferred strain. ATCC 53926 is the most preferred strain. ATCC 53926 is a mutant strain obtained by classical mutagenesis of *B. licheniformis* DSM 641 having the properties listed in Table II.

TABLE II

| Properties of *B. licheniformis* ATCC 53926 | |
|---|---|
| TAXONOMIC NAME | *B. licheniformis* ATCC 53926 |
| MORPHOLOGY | Vegetative Cells: |
| | Rods |
| | Width 0.7–0.9 m |
| | Length 2.0–3.0 m |
| | Spores: |
| | Ellipsoid |
| | Sporangium not swollen |
| MOBILITY | Motile |
| GRAM REACTION | Positive |
| CATALASE | Positive |
| ANAEROBIC GROWTH | Positive |
| VOGUES-PROSKAUER REACTION | Positive |
| | pH in Vogues-Proskauer medium: 5.5 |
| GROWTH PARAMETERS | TEMPERATURE |
| | Growth 50° C. |
| | No growth 55° C. |
| | pH: |
| | No growth pH 5.7 |
| | SALT TOLERANCE |
| | Grows in 5% NaCl |
| | Grows in 7% NaCl |
| | Grows in 10% NaCl |
| ACID PRODUCTION FROM: | Glucose positive |
| | L-Arabanose positive |
| | Xylose positive |
| | Mannitol positive |
| GAS PRODUCTION FROM GLUCOSE | Negative |
| LECITHINASE | Negative |
| HYDROLYSIS | Starch: Positive |
| | Gelatin: Positive |
| | Casein: Positive |
| ACID UTILIZATION | Citrate: Positive |
| | Propionate: Negative |
| TYROSINE DEGRADATION | Negative |
| INDOLE REACTION | Negative |
| PHENYLALANINE DEAMINASE | Negative |
| ARGININE DEHYDROLASE | Negative |
| NITRATE REDUCTION | Nitrate reduced to nitrite |

The gene coding for the BLAP enzyme can be obtained by isolating the chromosomal DNA from the *B. lentus* strain DSM 5483, constructing DNA probes having homology to putative DNA sequences encoding regions of the *B. lentus* protease, preparing genomic libraries from the isolated chromosomal DNA, and screening the libraries for the gene of interest by hybridization to the probes. The genomic libraries can be constructed in *E. coli* using plasmid pBR322, bacteriophage lambda EMBL3 and EMBL4, and the cosmid pCP13 as cloning vectors. Preferably, the gene bank of *B. lentus* DSM 5483 chromosomal DNA is constructed in *E. coli* with the cosmid pCP13.

Figure 24:
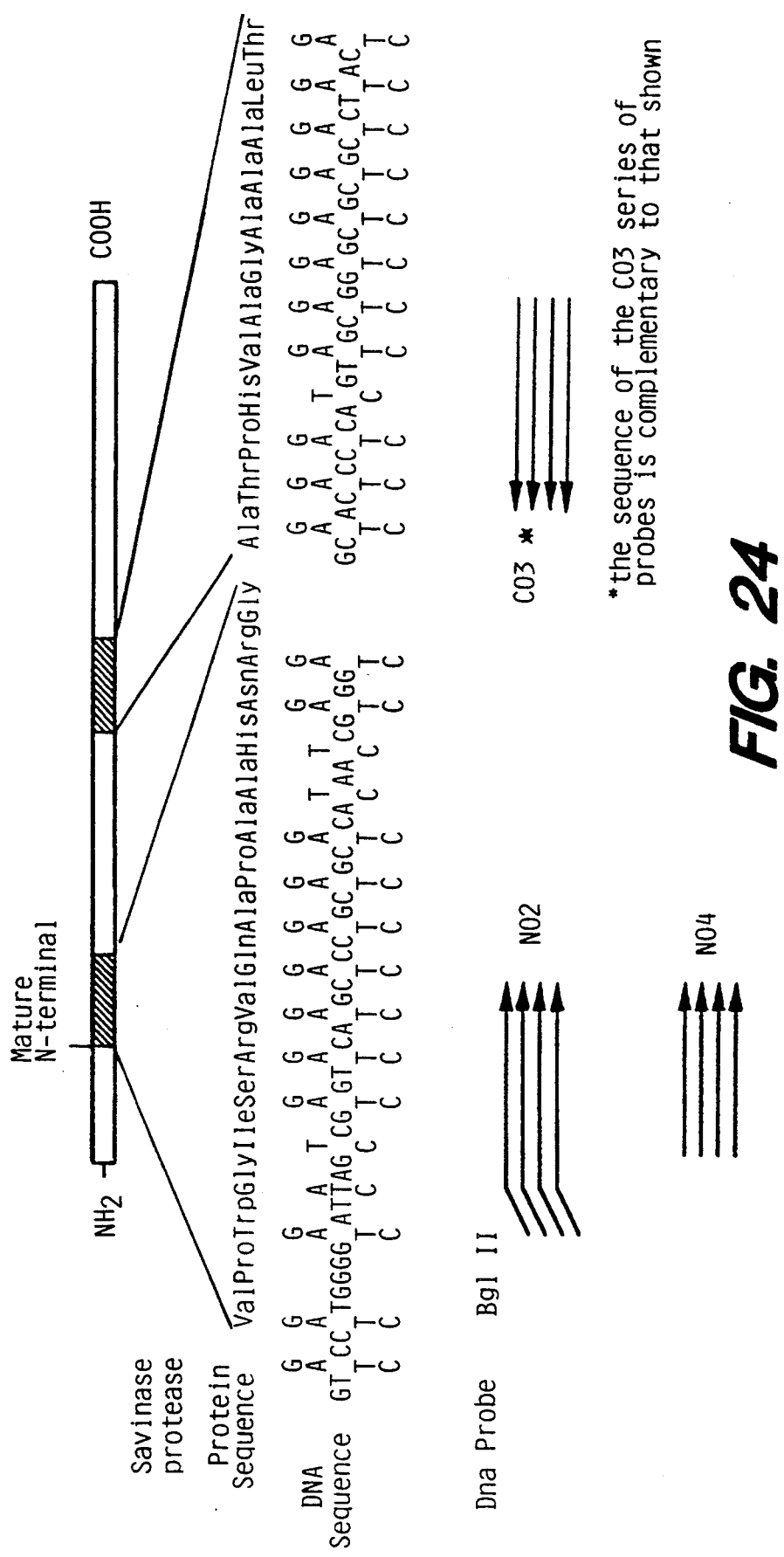
FIG. 24 shows a schematic diagram of the Savinase oligonucleotide probes. These probes were designed on the basis of known Savinase amino acid sequence to probe the *Bacillus lentus* gene banks and to serve as primers in the PCR reaction.

Oligonucleotide probes having DNA sequences similar to those of the Savinase gene (a gene encoding for Savinase, a commercial serine protease sold by Novo Industri A/S) can be used to probe for Savinase-like genes. Preferably, a BLAP sequence can be used. These oligonucleotides can be used to screen Southern blots of restriction enzyme digested chromosomal DNA's from *E. coli* HB101, *B. subtilis* DB104, *B. licheniformis*, and the *B. lentus* strain. The N-terminal and internal oligonucleotides as shown in FIGS. 24 and 25 can also be utilized as primers in the PCR to amplify that region of *B. lentus* chromosomal DNA extending from the N-terminus of the mature alkaline protease to the N-terminus of the C-terminal cyanogen bromide fragment.

A portion of the mature region of the alkaline protease gene can be isolated by constructing a larger, double stranded DNA probe specific for the *B. lentus* alkaline protease using the PCR. An analysis based on the amino acid sequence for the C-terminal cyanogen bromide fragment from the Savinase protease shows that this sequence has homology with the amino acid sequence around the active site serine of Savinase, as well as other subtilisin type serine proteases. The amplified fragment is approximately 650 basepairs (bp) in length, in agreement with the expected size estimated from sequence data available for other Bacillus alkaline proteases. The 650 bp PCR fragment represents a portion of a gene encoding an alkaline protease, beginning just after the N-terminus of the mature protease and continuing into the protein coding region.

The 650 bp fragment can be used to identify the BLAP gene in the genomic library. After purification, the 650 bp fragment can be labeled for example by nick translation and used to probe gene banks of *B. lentus* DSM 5483 DNA which may be constructed by using the cosmid pCP13 and EMBL lambda vectors. Several cosmid clones carrying DNA with homology to the 650 bp PCR fragment and to selective oligonucleotide probes may then be identified. Plasmid DNA of one of these cosmids, pHSH44, has been purified and characterized by restriction enzyme analysis. Results from Southern analysis show that a *B. lentus* DSM 5483 HindIII fragment of approximately 3.4 kb can hybridize to the radioactively labeled probes 650 bp PCR fragment. The hybridization, restriction analyses and DNA sequence (FIG. 2) show that the 3.4 kb HindIII fragment having homology to the 650 bp PCR fragment encodes the BLAP gene.

The fermentation of ATCC 53926 containing an expression cassette which is based on gene fusions comprising parts of the ATCC 53926 alkaline protease gene and parts of the BLAP gene is used in the preferred method of making BLAP on a large scale production basis. Such a cassette consists of a regulatory region from the ATCC 53926 alkaline protease gene comprised of a promoter, ribosome binding site and initiation codon which is responsible for the efficient transcription and translation of the corresponding gene. The regulatory region is followed by a DNA sequence coding for the signal (pre) peptide, followed by sequences encoding the pro-peptide and the mature protease. After transcription of the DNA sequence downstream from the promoter, the messenger-RNA (m-RNA) is translated into the pre-pro-mature protease, which consists of the signal peptide, the pro peptide and the mature protease. The signal sequence directs the immature protease through the cytoplasmic membrane, where the signal peptide is cleaved off enzymatically by a signal peptidase. The pro sequence seems to insure correct folding and processing of the pro-protease during or after translocation across the cytoplasmic membrane and the cell wall, releasing the mature protease (Power, S. D. et al. (1986) PNAS(U.S.A.), 83, 3096; Ikemura, H. et al. (1987) J. Biol. Chem. 262, 7859; Ikemura, H. et al. (1988) J. Biol. Chem. 263, 12959).

Two fusion types identified by the restriction enzyme sites used to join different portions of the ATCC 53926 alkaline protease gene and BLAP genes together can be used to prepare the previously described expression cassettes which when used to transform ATCC 53926 will produce BLAP enzyme on a commercial scale. These cassettes are made from ClaI and NcoI fusions.

The ClaI fusion combines the ATCC 53926 alkaline protease gene promoter and pre sequence with a DNA fragment encoding the pro and mature sequence of BLAP. A ClaI restriction site can be introduced into the ATCC 53926 alkaline protease gene several codons upstream from the junction of the ATCC 53926 alkaline protease pre and pro sequence. The BLAP gene contains a naturally occurring ClaI site at this position. The promoter and most of the pre region of the ATCC 53926 alkaline protease gene (AvaI/ClaI DNA fragment) can be fused to the (ClaI/SstI) fragment of the BLAP gene which contains a portion of the pre region and all of the pro and mature BLAP sequence. The NcoI and ClaI fusions can be made in *E. coli* and subcloned into two different Bacillus vectors on an AvaI/SstI DNA fragment.

The NcoI fusion produces a mature protease slightly different from the BLAP. The protein made from the NcoI fusion contains threonine at position 3 from the N-terminus of the mature protease while the BLAP contains serine at the same position (FIG. 29). The NcoI fusion can be constructed by combining the promoter, pre and pro sequences of the ATCC 53926 alkaline protease gene with the mature sequence of the BLAP gene. A NcoI restriction site can be introduced into the ATCC 53926 alkaline protease gene several codons downstream from the junction of the pro and mature sequence. A naturally occurring NcoI site is present at a similar position in the BLAP gene. Then, the promoter, pre, pro and four codons of the mature ATCC 53926 sequence (AvaI/NcoI DNA fragment) can be fused to a mature BLAP sequence missing the first four codons (NcoI/SstI DNA fragment). The NcoI and ClaI fusions can be made in *E. coli* and subcloned into two different Bacillus vectors on an AvaI/SstI DNA fragment.

To further increase enzyme production the ClaI and NcoI fusions can be cloned either with a ATCC 53926 alkaline protease transcription terminator cassette which is a 164 bp DNA fragment, or with a 608 bp C-terminal fragment from the ATCC 53926 alkaline protease gene which is discussed in more detail below.

Figure 4:
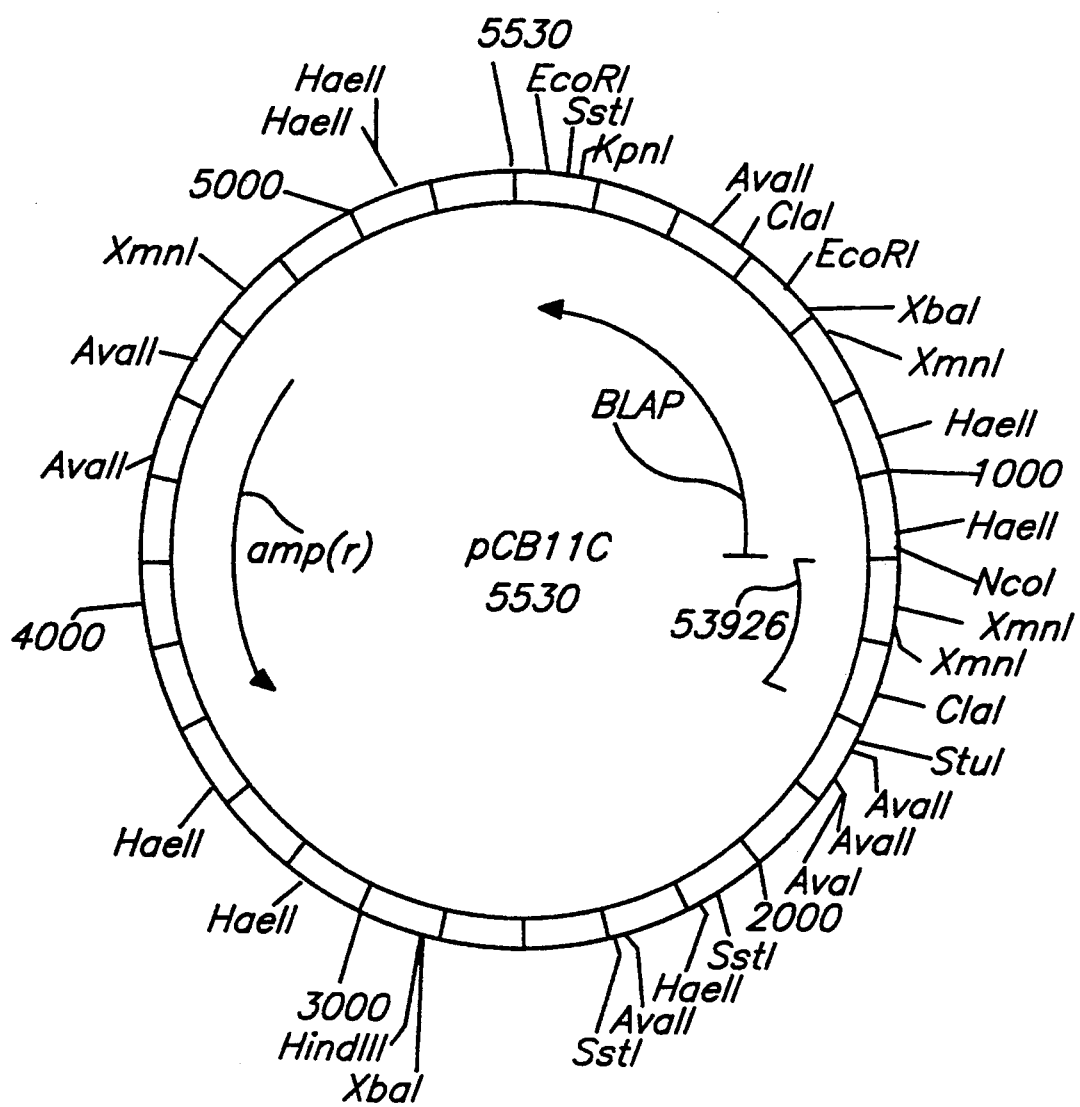
FIG. 4 shows the restriction map for plasmid pCB11C.
Figure 5:
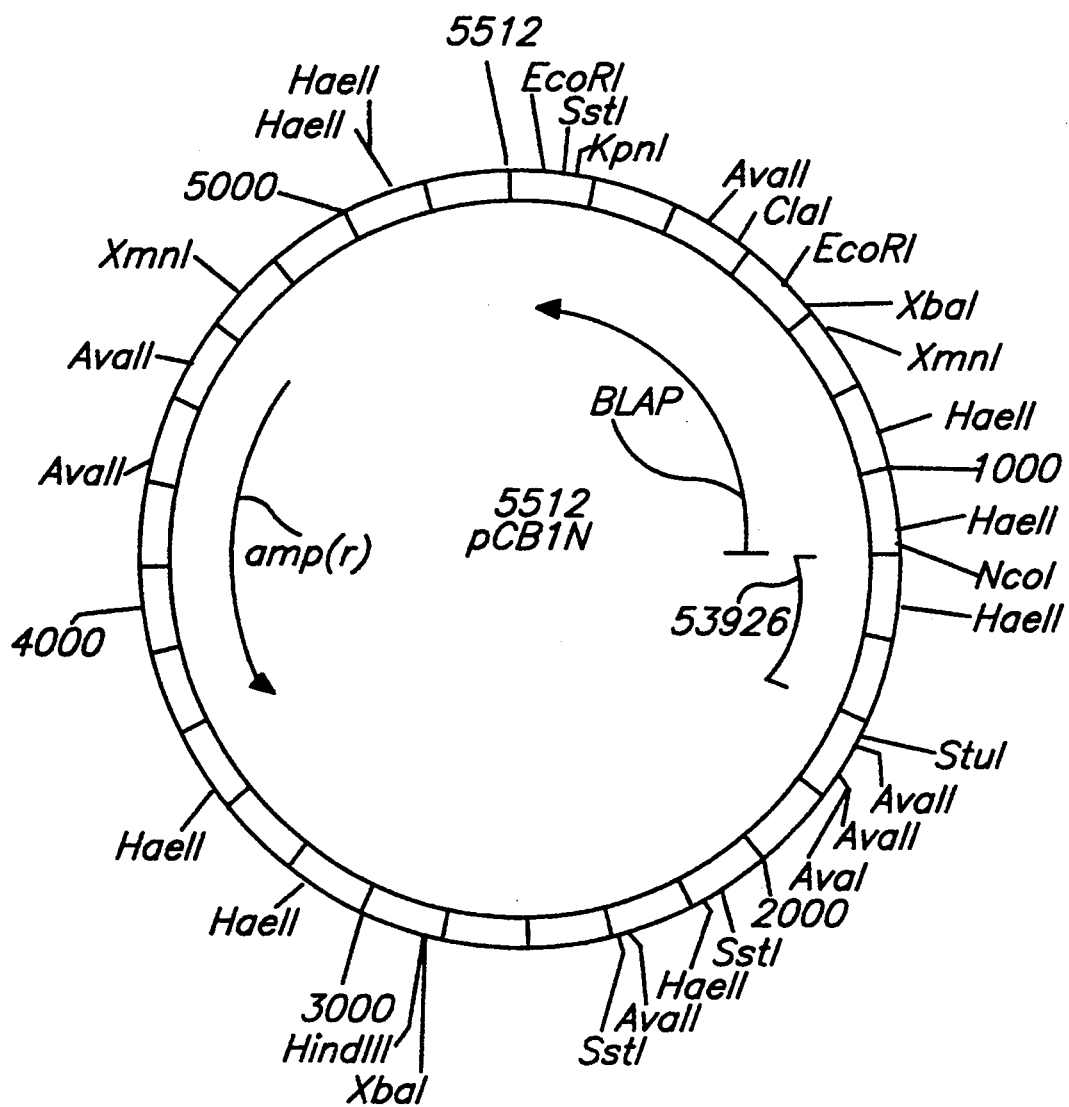
FIG. 5 shows the restriction map for plasmid pCB1N.
Figure 6:
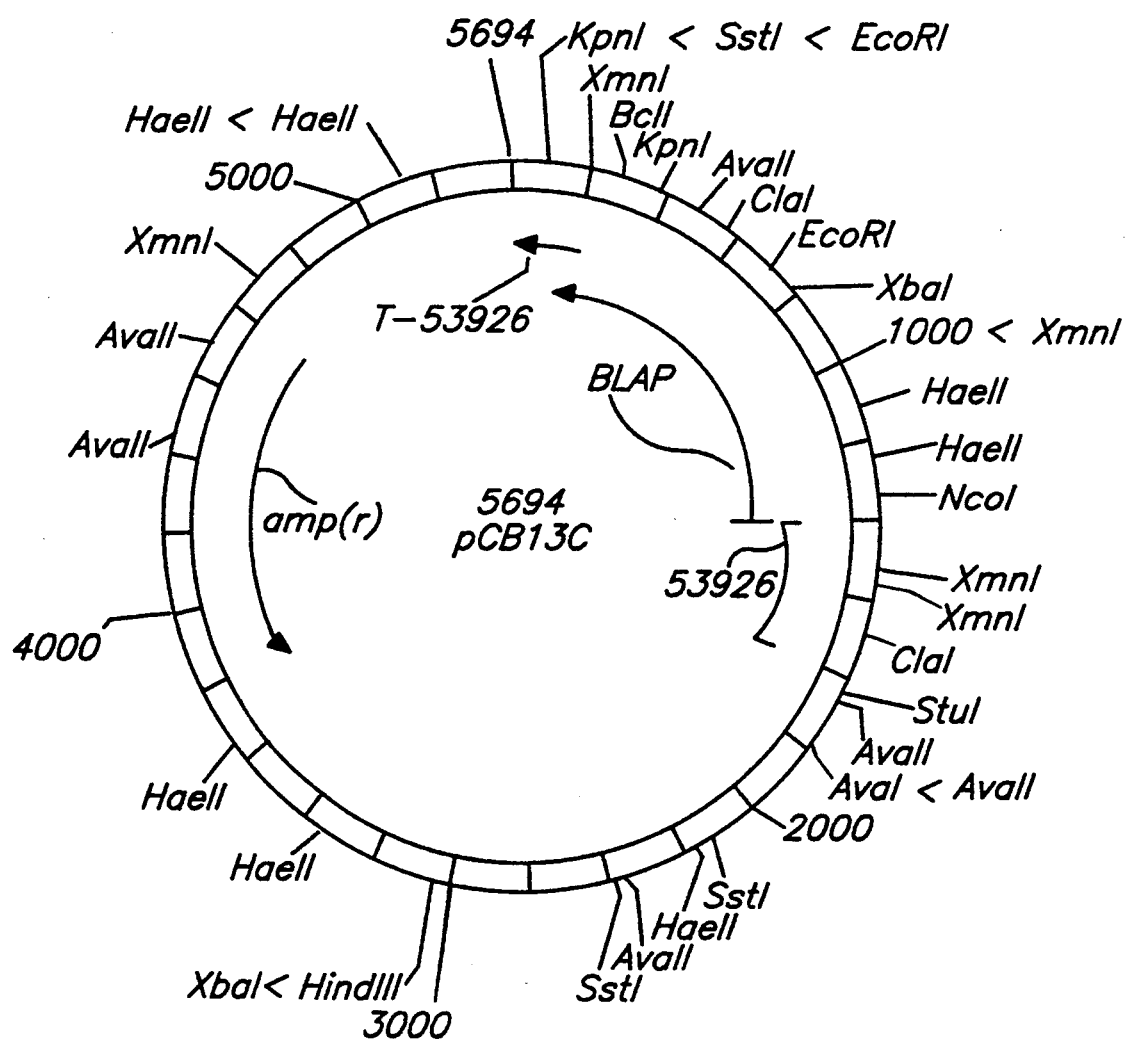
FIG. 6 shows the restriction map for plasmid pCB13C.
Figure 7:
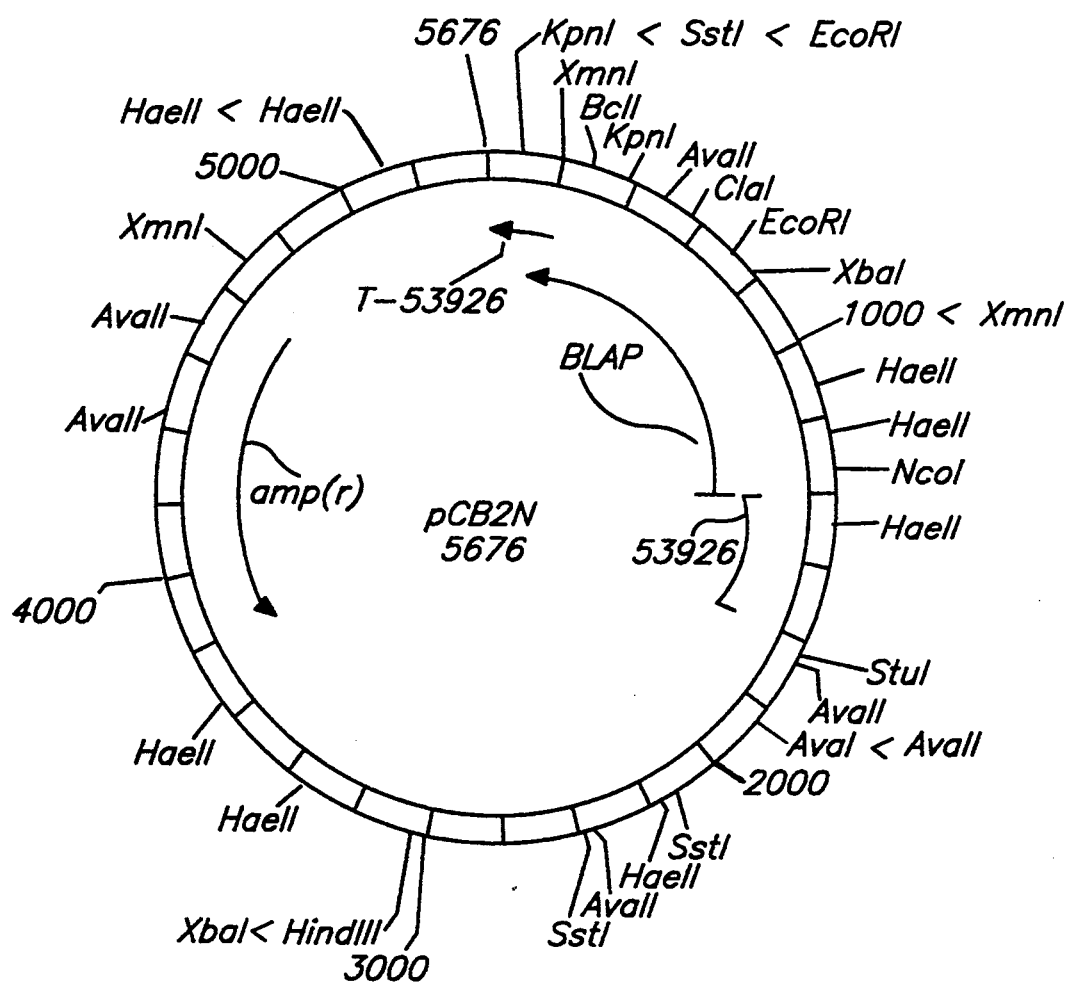
FIG. 7 shows the restriction map for plasmid pCB2N.
Figure 9:
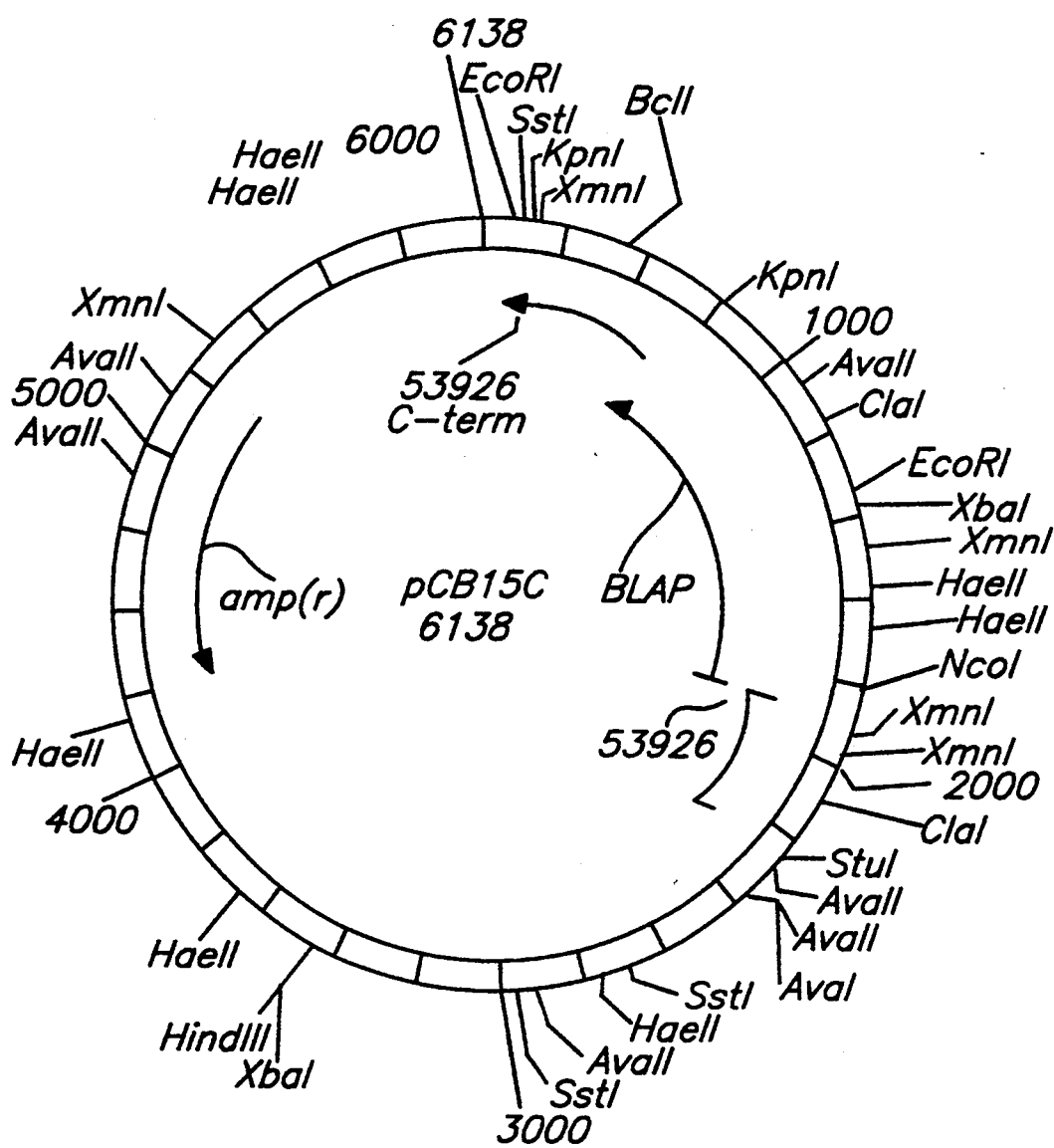
FIG. 9 shows the restriction map for plasmid pCB15C.
Figure 10:
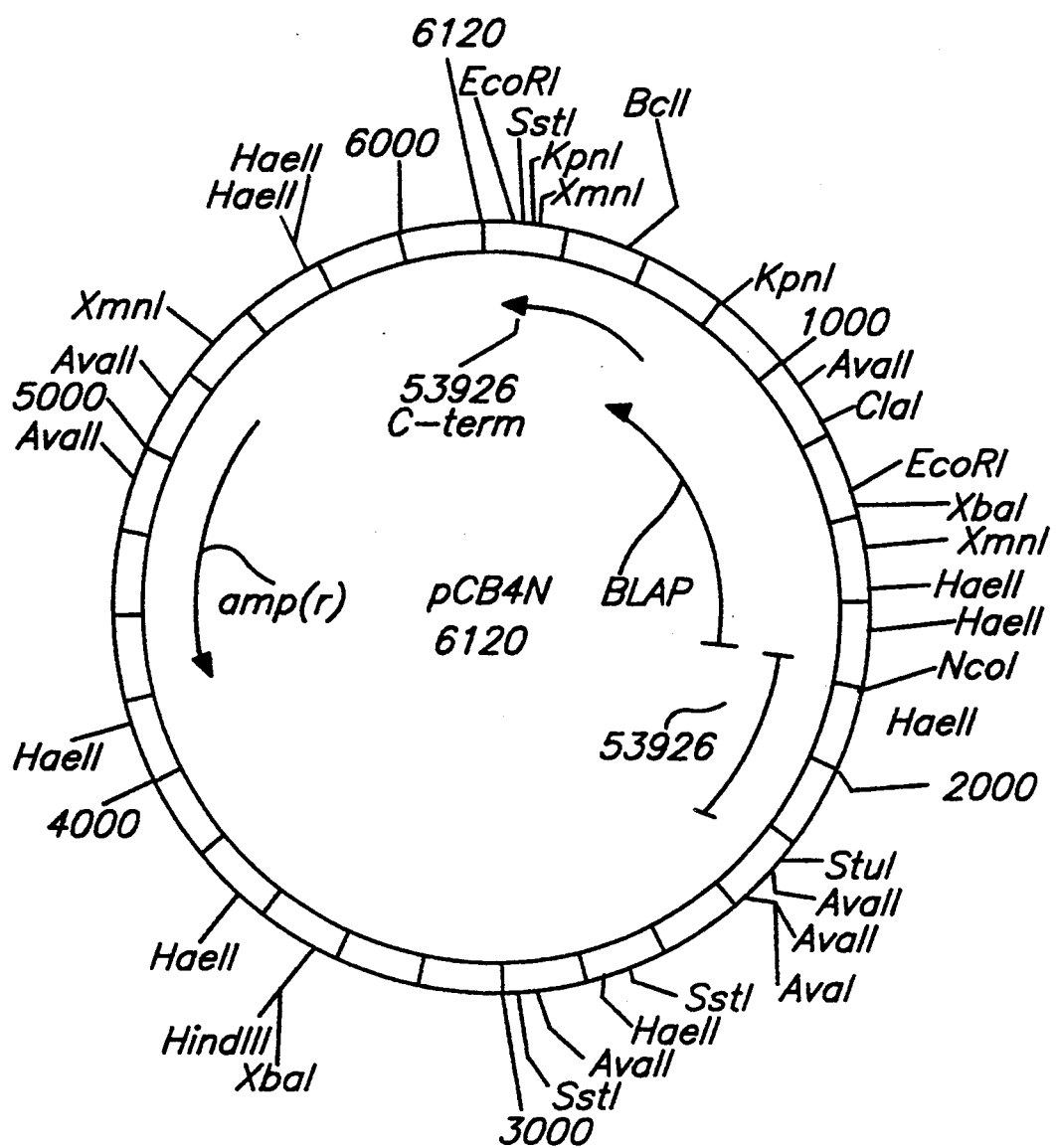
FIG. 10 shows the restriction map for plasmid pCB4N.
Figure 11:
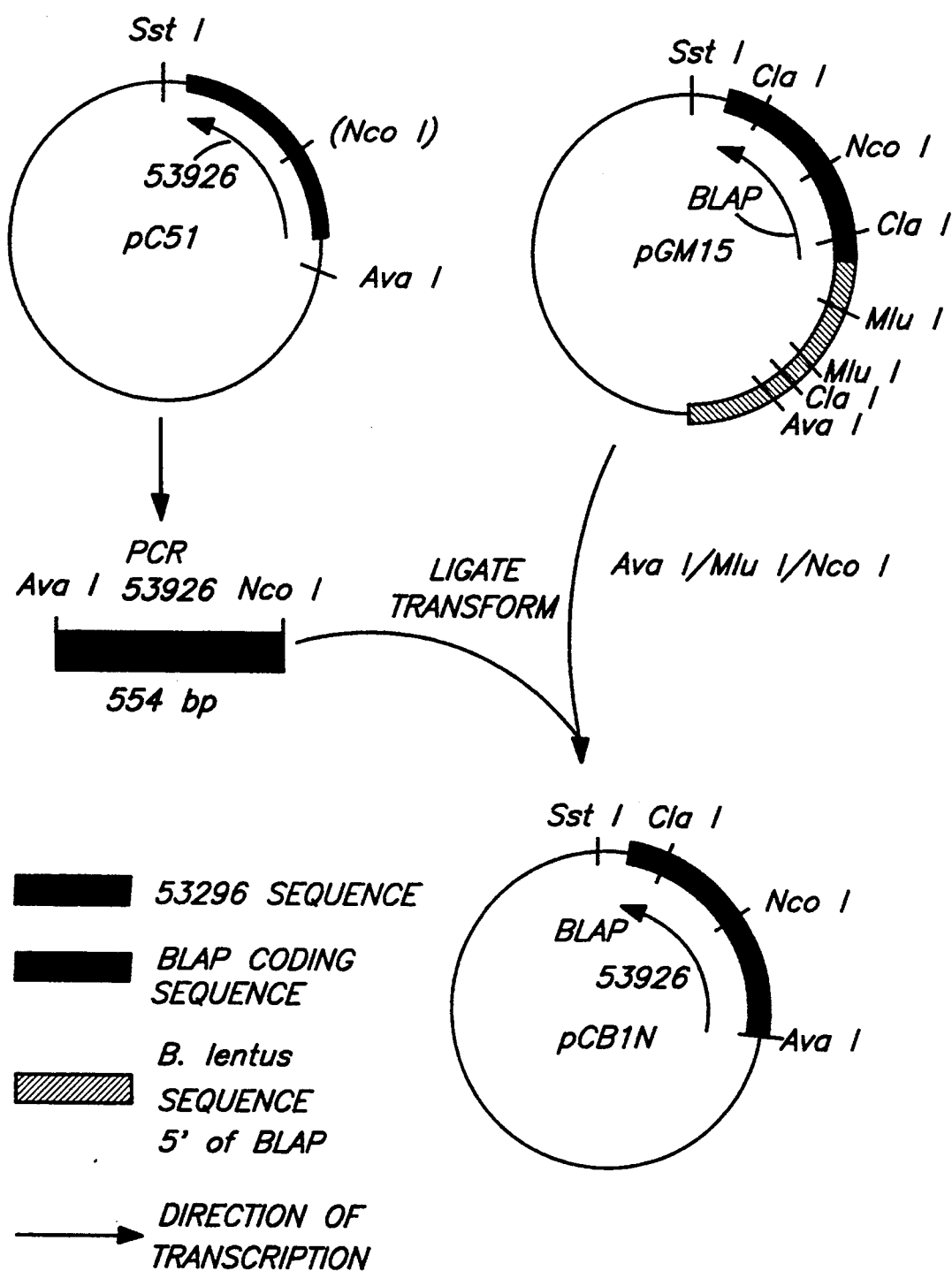
FIG. 11 shows a scheme for the construction of plasmid pCB1N.
Figure 12:
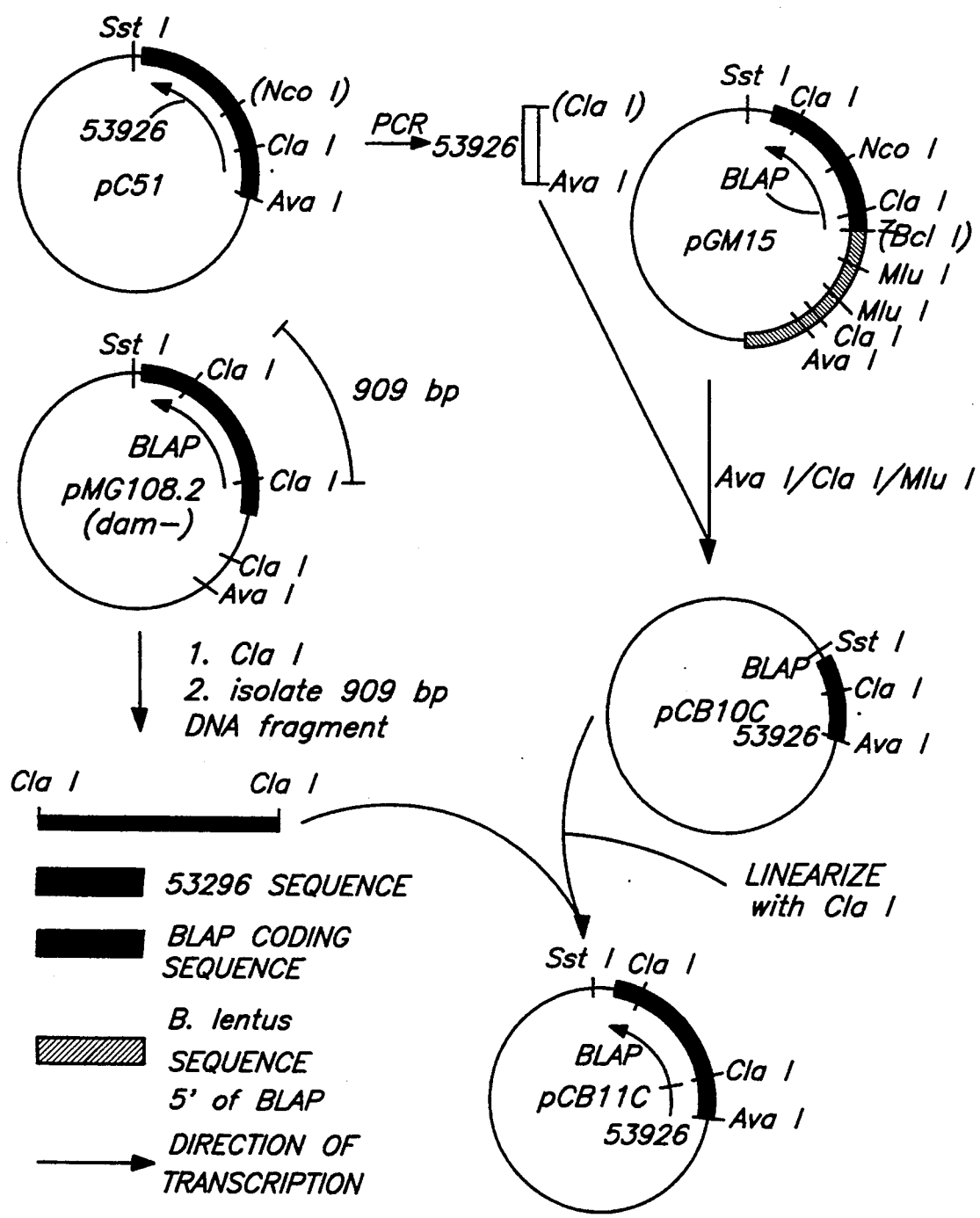
FIG. 12 shows a scheme for the construction of plasmid pCB11C.
Figure 13:
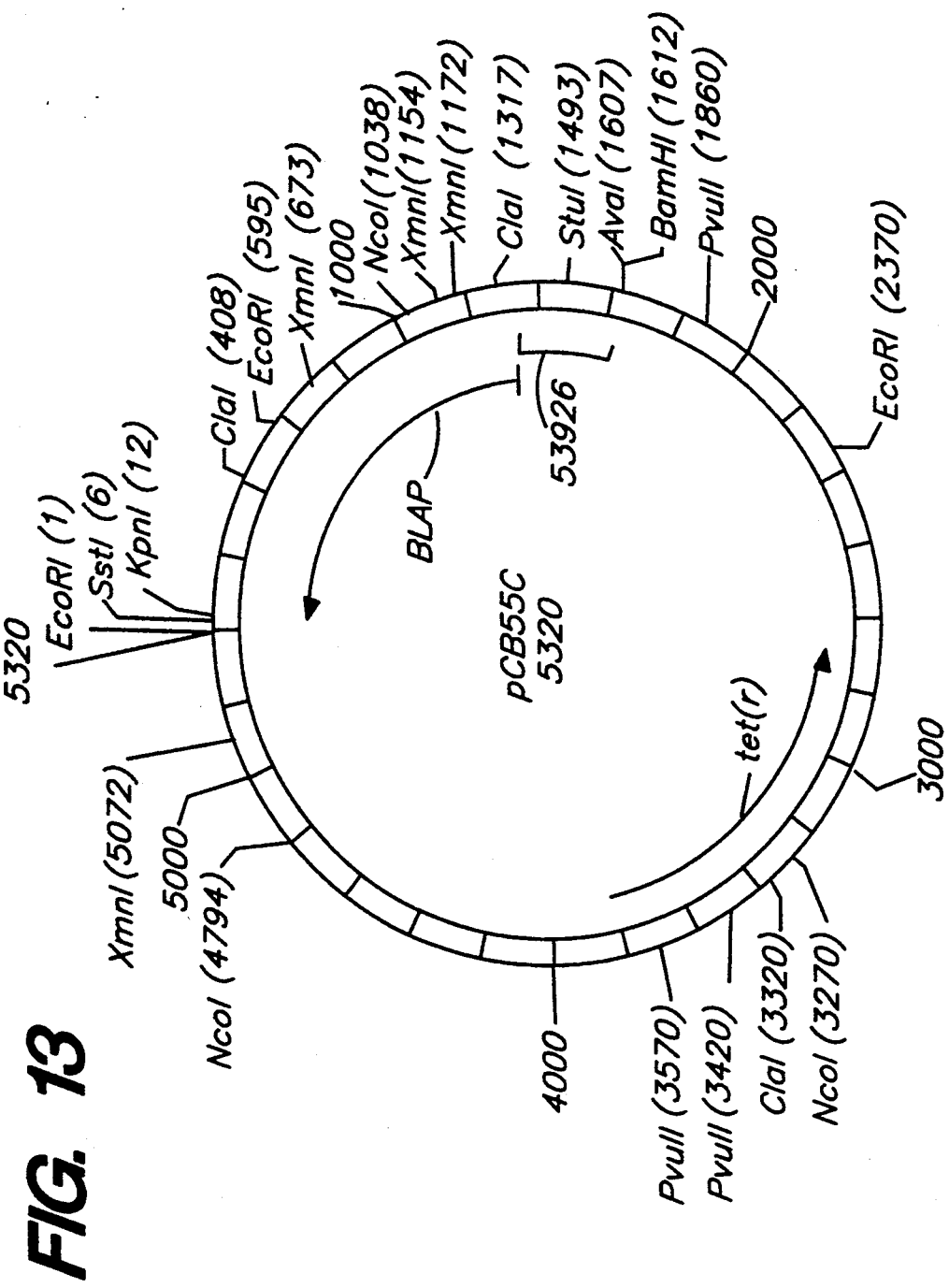
FIG. 13 shows the restriction map for plasmid pCB55C.
Figure 14:
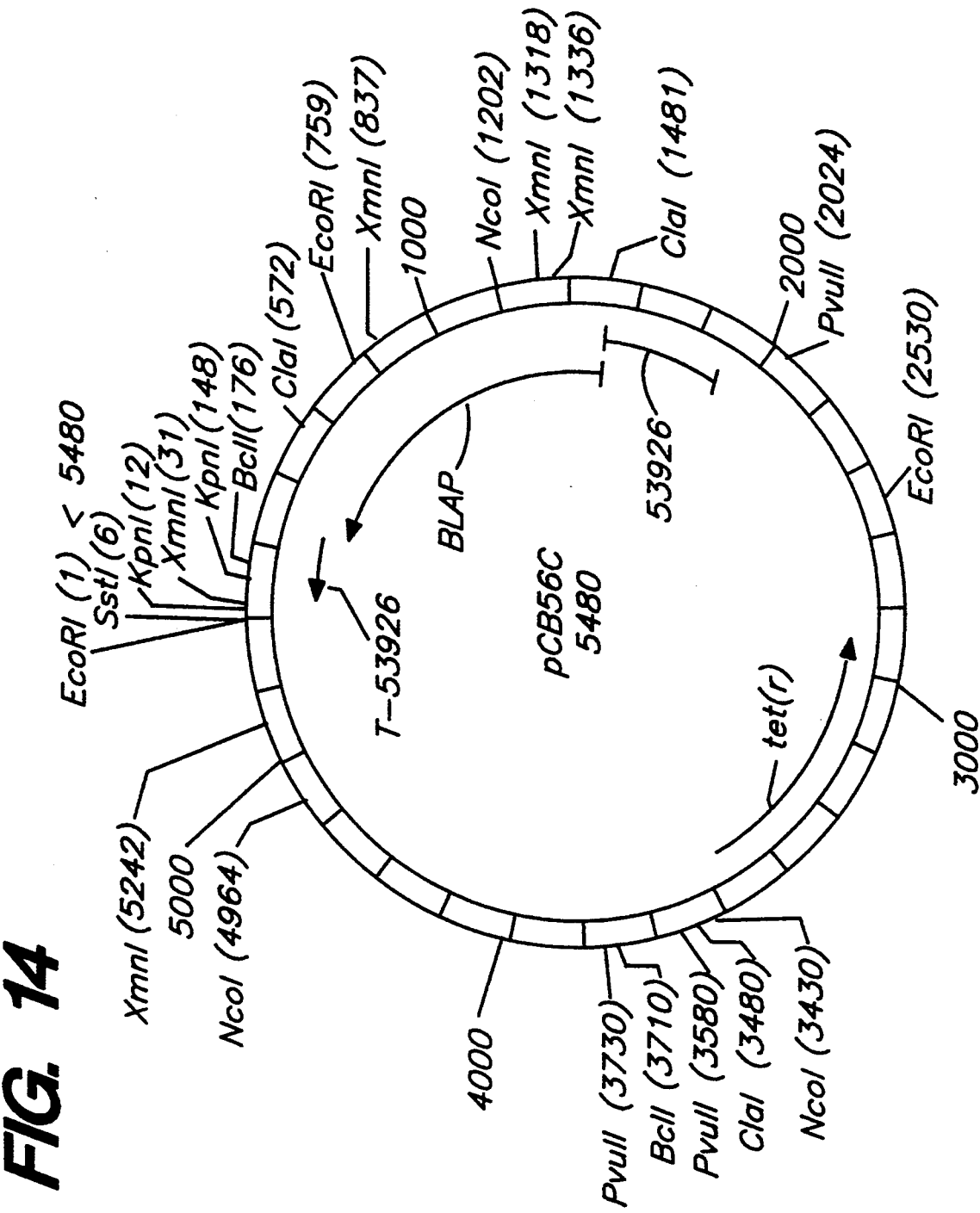
FIG. 14 shows the restriction map for plasmid pCB56C.
Figure 15:
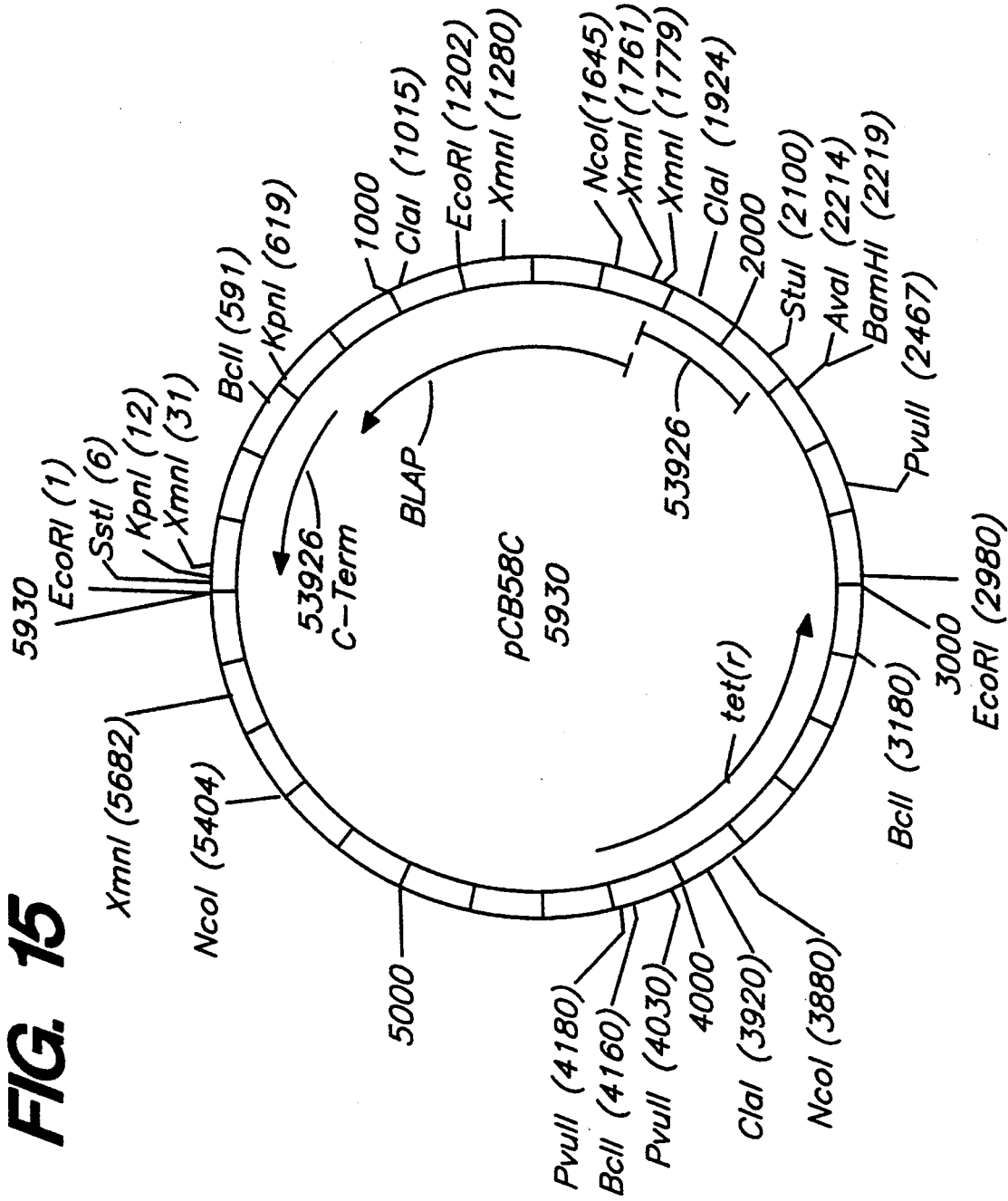
FIG. 15 shows the restriction map for plasmid pCB58C.
Figure 16:
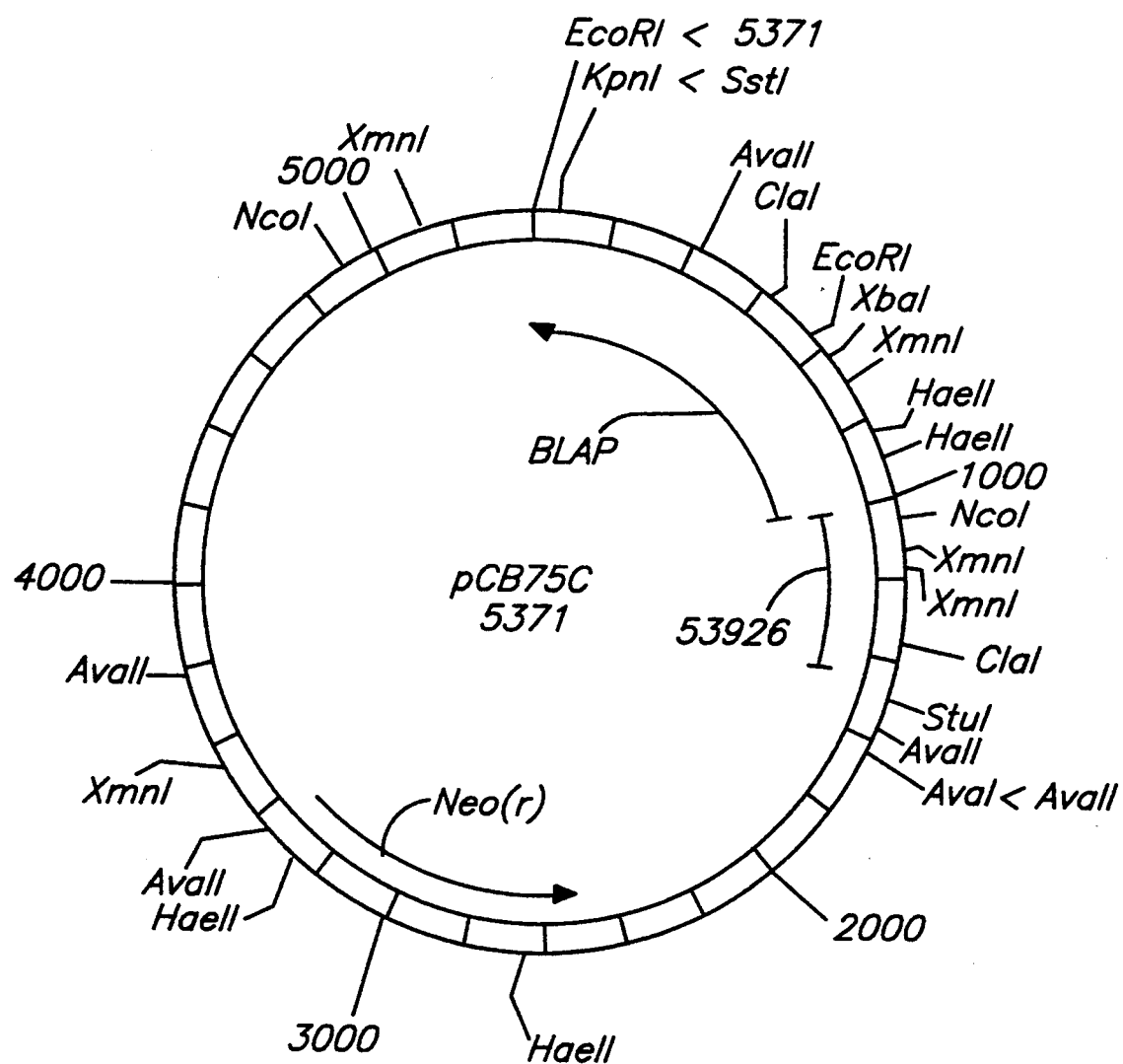
FIG. 16 shows the restriction map for plasmid pCB75C.
Figure 17:
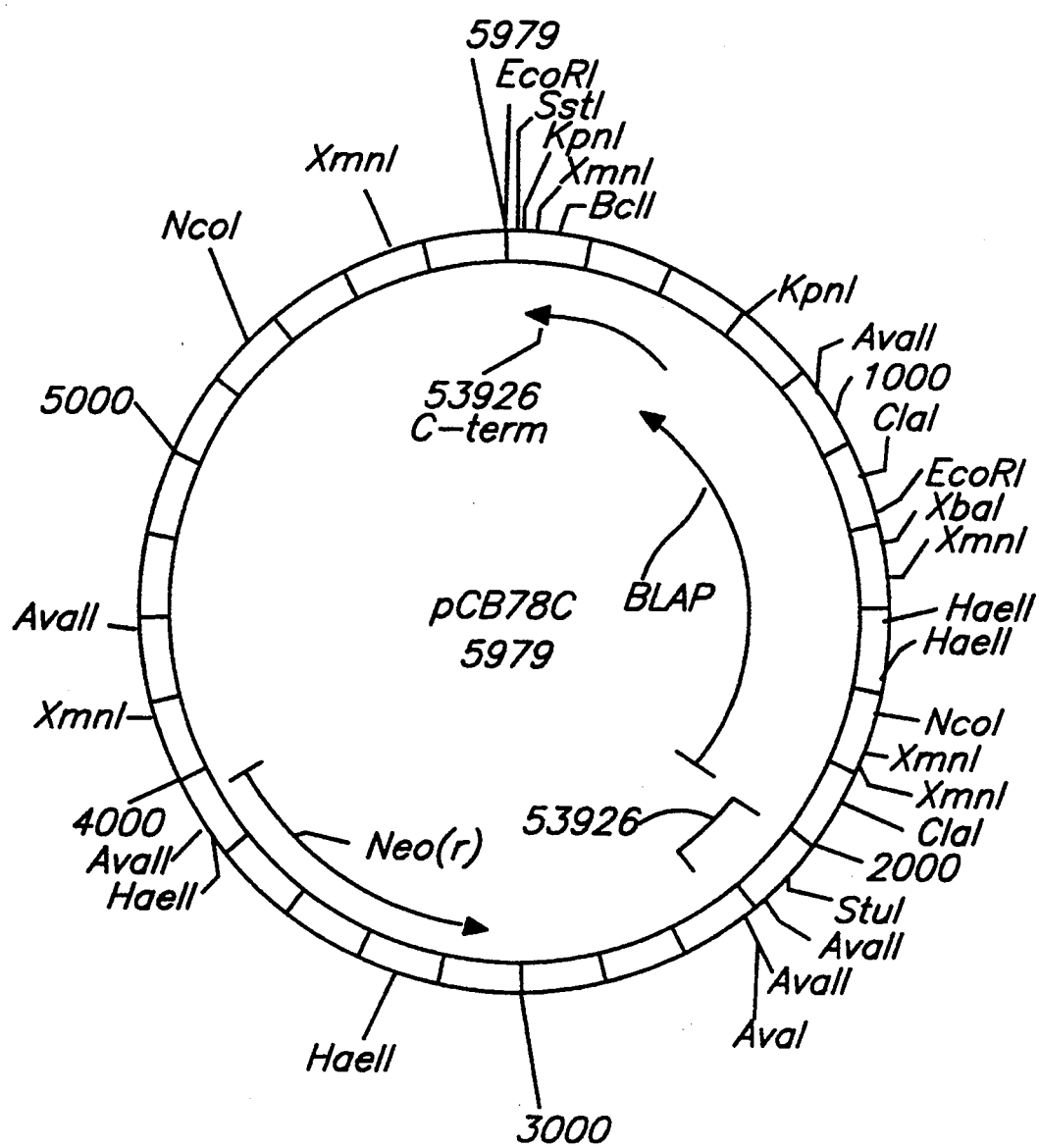
FIG. 17 shows the restriction map for plasmid pCB78C.
Figure 18:
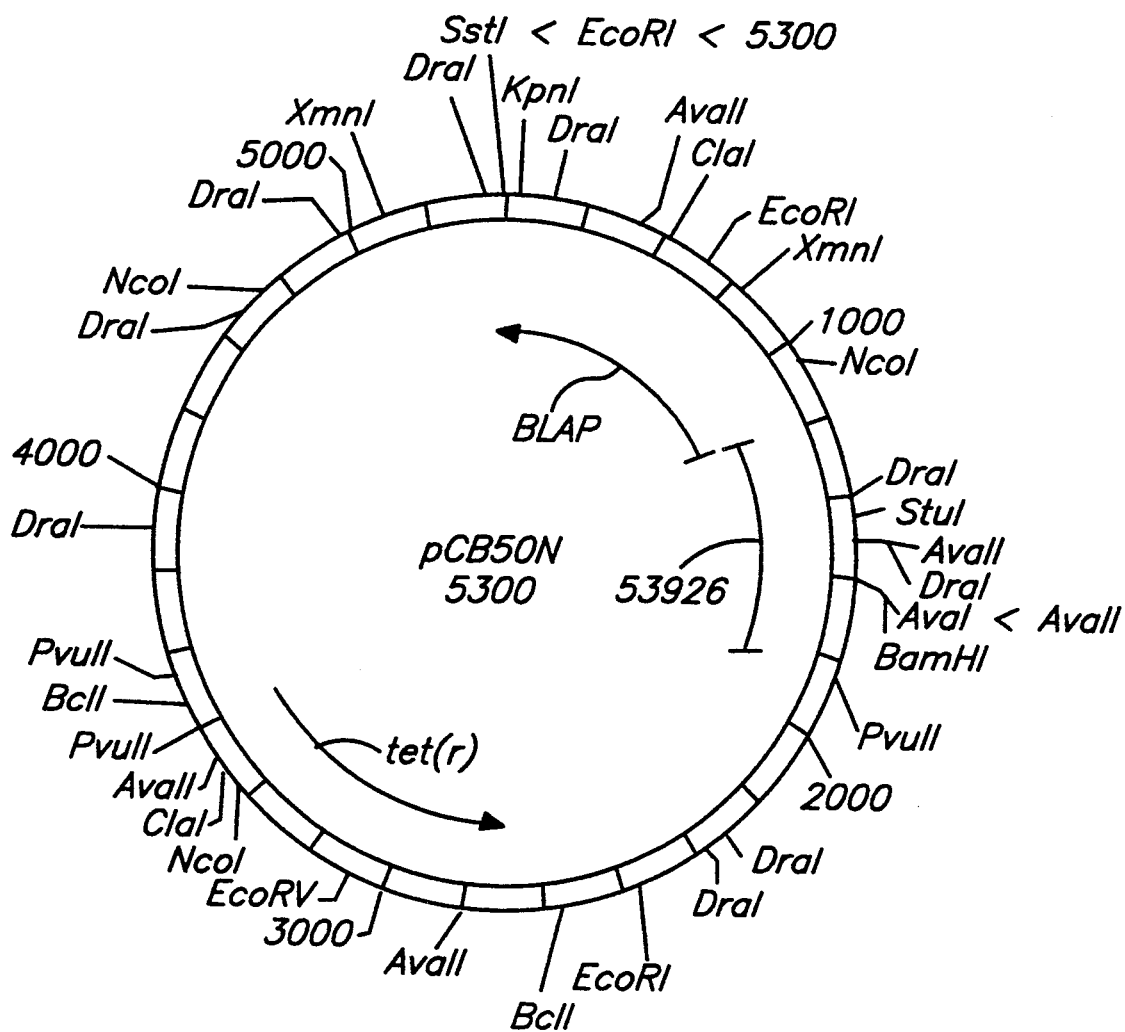
FIG. 18 shows the restriction map for plasmid pCB50N.
Figure 19:
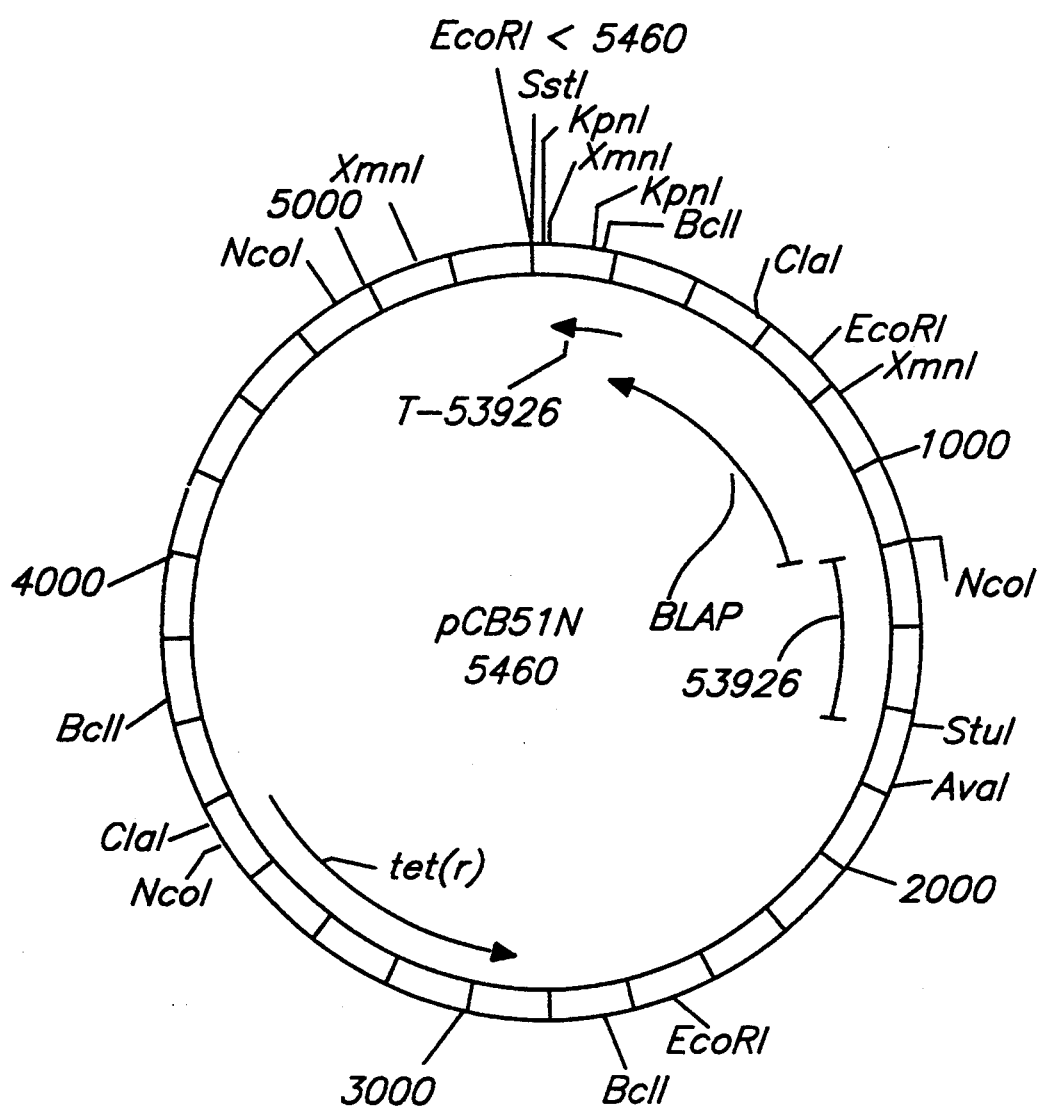
FIG. 19 shows the restriction map for plasmid pCB51N.
Figure 20:
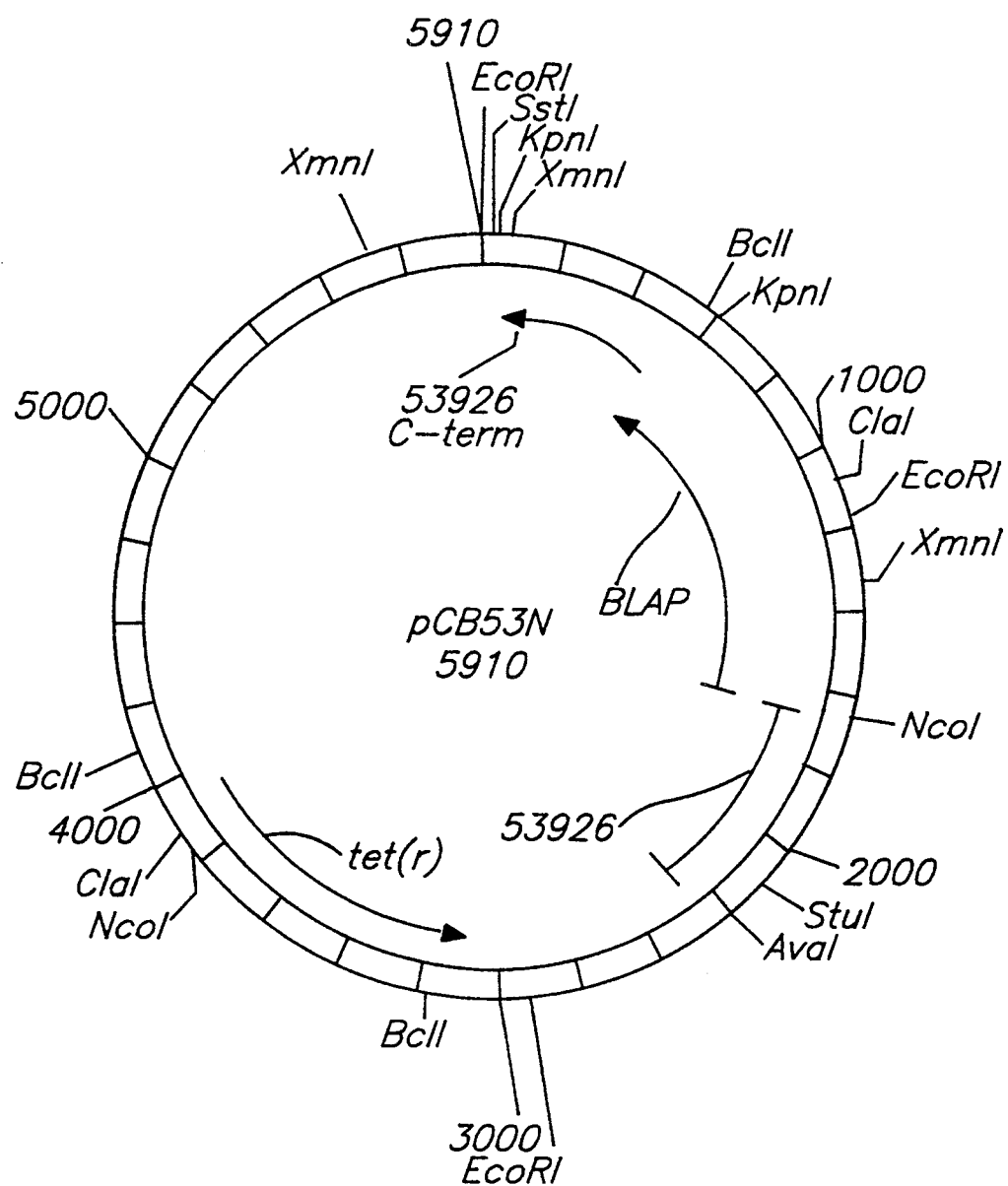
FIG. 20 shows the restriction map for plasmid pCB53N.
Figure 21:
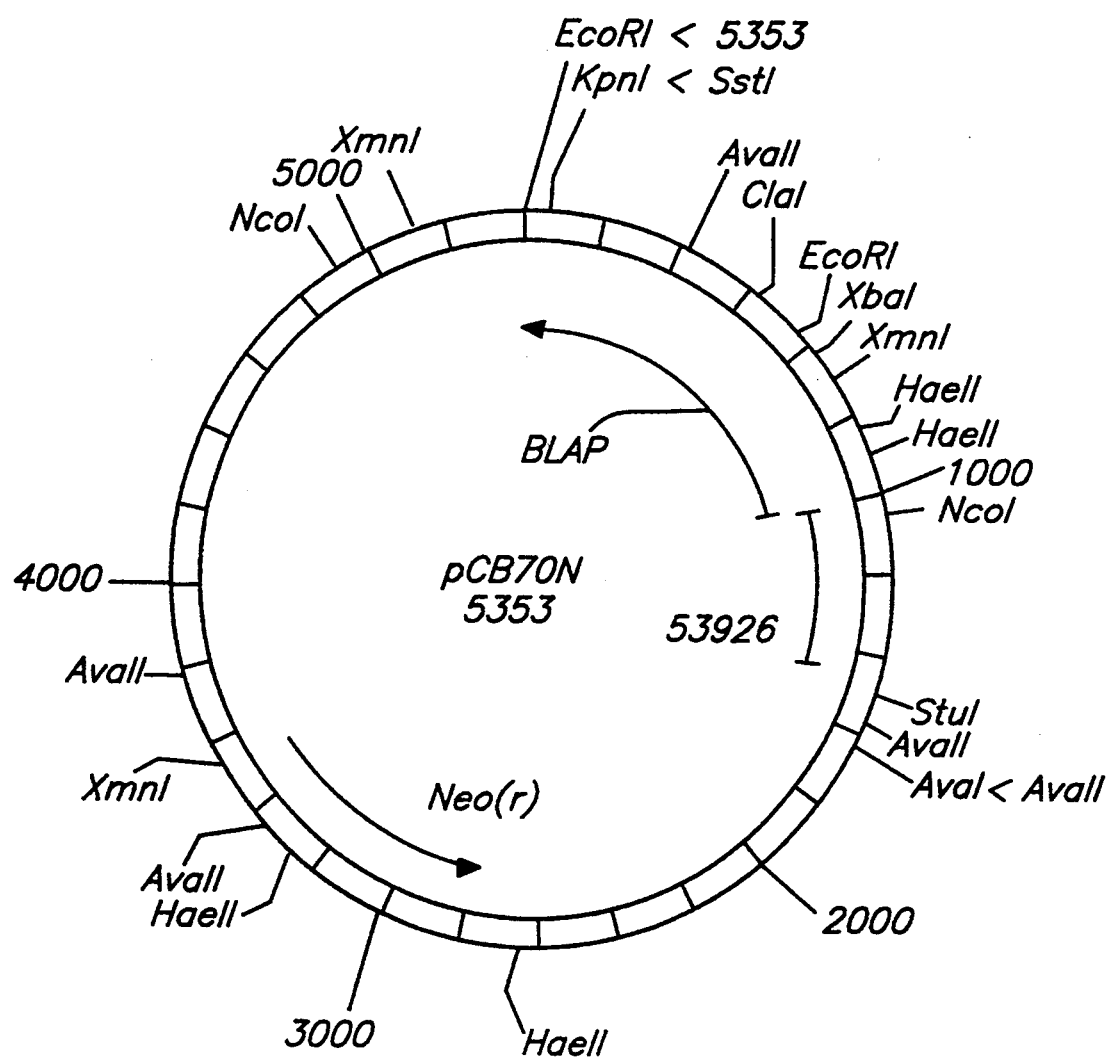
FIG. 21 shows the restriction map for plasmid pCB70N.
Figure 22:
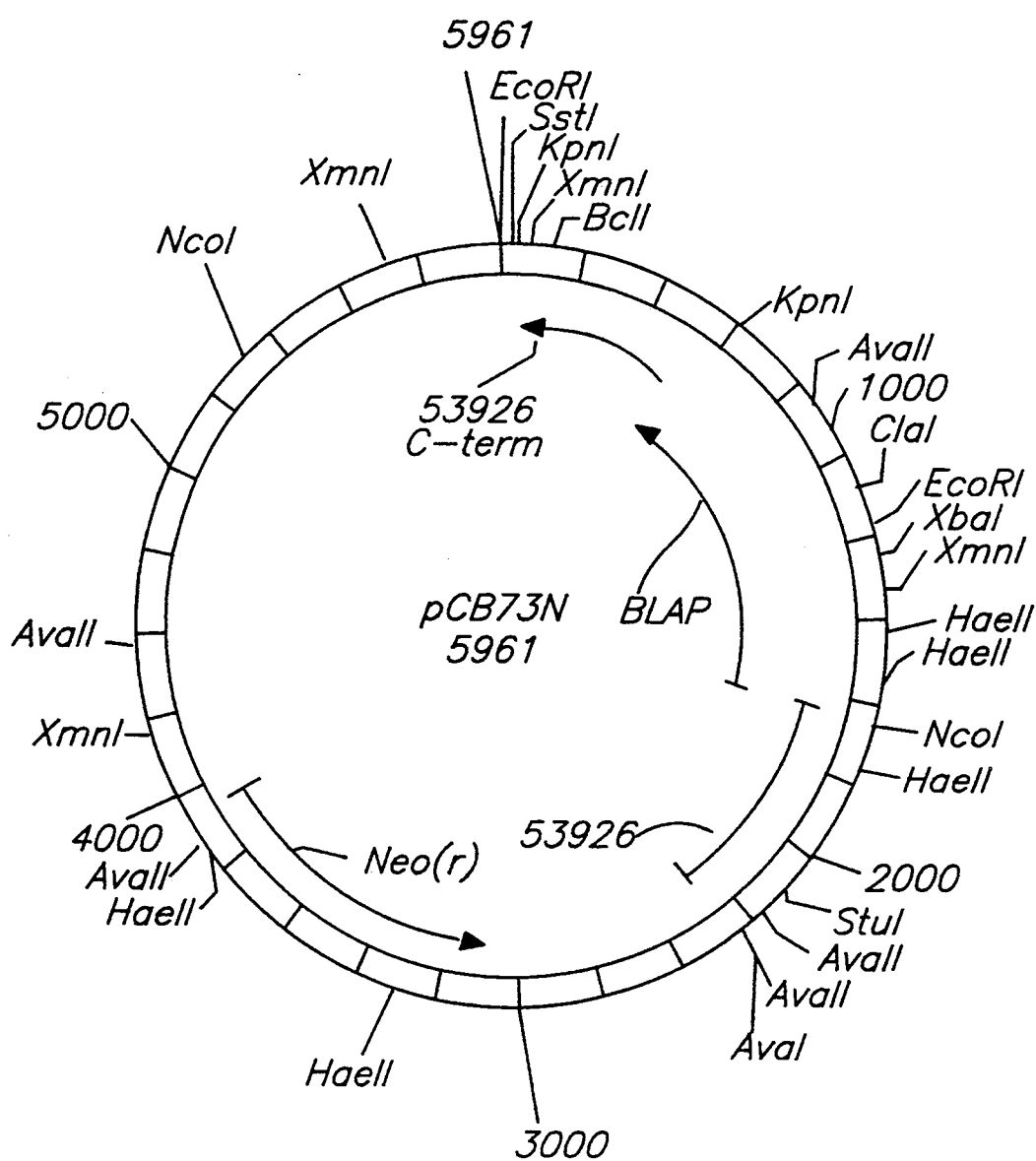
FIG. 22 shows the restriction map for plasmid pCB73N.

The ATCC 53926 alkaline protease-BLAP fusion genes can be constructed in the *E. coli* vector pGM15 (FIG. 3), a pTZ19R derivative that contains the 3.4 kb HindIII/KpnI fragment containing the BLAP gene, and then subcloned into Bacillus vectors pBC16 and pUB110. Bacillus fusion gene vector pCB1N (FIG. 5) is constructed as shown in FIG. 11. Bacillus fusion gene vector pCB11C (FIG. 4) can be constructed as shown in FIG. 12. Variations of each of the gene fusions described above can be prepared in order to: (a) provide more effective expression of the BLAP protease gene, and (b) to ensure suppression of the expression of the chromosomally encoded ATCC 53926 alkaline protease gene. In order to provide effective termination of the transcription of the BLAP protease gene, the ATCC 53926 alkaline protease transcription terminator can be cloned as a 164 bp DNA fragment downstream of the BLAP terminator in each of the gene fusions described above. Constructs carrying the ATCC 53926 alkaline protease transcription terminator cassette in the same orientation relative to the transcription of the ATCC 53926 alkaline protease-BLAP fusion gene in plasmids pCB11C and pCB1N are designated pCB13C and pCB2N (FIG. 6 and 7) respectively. In order to suppress the expression of the chromosomally encoded ATCC 53926 protease gene, two additional Bacillus BLAP fusion gene vectors containing a C-terminal fragment of the ATCC 53926 alkaline protease gene can be constructed in plasmids pCB11C and pCB1N by ligating a 608 bp fragment of the ATCC 53926 alkaline protease gene synthesized by the PCR using plasmid pC51 as template. The 608 bp DNA fragment can be ligated into the single KpnI site present on vectors pCB11C and pCB1N and new constructs containing the 608 bp ATCC 53926 C-terminal fragment in the same orientation relative to the direction of transcription of the ATCC 53926 alkaline protease-BLAP fusion genes in pCB11C and pCB1N are designated pCB15C and pCB4N respectively. Restriction maps of these plasmids are given in FIGS. 9 and 10 respectively.

The six ATCC 53926 alkaline protease-BLAP fusion genes described above and listed below can be subcloned into Bacillus vectors and transformed into *B. subtilis* DB104. The ATCC 53926 alkaline protease-BLAP fusion genes can be subcloned as AvaI/SstI DNA fragments into pBC16 and pUB110 derivatives by digesting the *E. coli* vectors containing the ATCC 53926 alkaline protease-BLAP fusion genes (pCB1N, pCB11C, pCB2N, pCB13C, pCB4N and pCB15C) with AvaI and SstI, and ligating them to Bacillus plasmids pC51 and pH70 which have been restricted with AvaI, SstI, PstI and SalI. Plasmids pC51 and pH70 were cut with AvaI/SstI to provide the large AvaI/SstI vector fragment containing the necessary origin of replication and an antibiotic resistance gene (tetracycline resistance in pC51, kanamycin resistance in pH70) for selection. SalI and PstI can be used to restrict the small AvaI/SstI fragment containing the entire ATCC 53926 alkaline protease gene present on pC51, and pH70 into three smaller DNA fragments. This decreases the probability of religating the ATCC 53926 alkaline protease gene into the Bacillus vectors.

A total of ten ATCC 53926 alkaline protease-BLAP gene fusion plasmids constructed as described above derived from the ClaI and NcoI fusions can be realized in ATCC 53926. Five Bacillus plasmid constructs derived from the six ClaI fusions can be transformed into the ATCC 53926 strain. These Bacillus plasmids are pCB55C, pCB56C, pCB58C, pCB75C, and pCB78C (FIGS. 13, 14, 15, 16, and 17 respectively). Five Bacillus plasmid constructs derived from the six NcoI fusions can be transformed into the ATCC 53926 strain. These Bacillus plasmids are pCB50N, pCB51N, pCB53N, pCB70N, and pCB73N (FIGS. 18, 19, 20, 21, and 22 respectively).

For production of the greatest protease yields, the ATCC 53926 strain carrying the ClaI fusion constructs (FIG. 23) inserted into a pC51 derivative is preferred. Construct pCB58C (FIG. 15) in the ATCC 53926 strain is the most preferred embodiment for producing the greatest protease yields.

The fermentations can be carried out in complex nutrient media generally known to those skilled in the art. These media can contain such carbon sources as glucose, sucrose, and/or corn starch. The media can also contain such nitrogen sources as soy bean meal, cottonseed meal, casein and potatoe extract. Other growth promoting ingedients include brewing residue, and corn steep liquor and inorganic materials such as inorganic phosphates. The media can also contain antifoams.

A comparison of the relative protease yields of the different ATCC 53926 alkaline protease-BLAP constructs in the ATCC 53926 production strain is shown in FIG. 28. These fermentations were performed with antibiotic selection, using a complex production medium containing 0.5% nitrogen. Protease yields of the ATCC 53926 alkaline protease-BLAP constructs are presented relative to ATCC 53926 containing plasmid pAM2.3. This plasmid contains the native BLAP promoter and structural gene on an NruI/SalI restriction fragment inserted into plasmid pC51 between the StuI/SalI sites.

The fermentation broths obtained by cultivating the different ATCC 53926 alkaline protease-BLAP constructs in the ATCC 53926 production strain typically contain other proteolytic enzymes. However, the BLAP protease in the fermentation broths obtained by fermentation of the different ATCC 53926 alkaline protease-BLAP constructs in the ATCC 53926 production strain is the major proteolytic enzyme in the broths. These fermentation broths contain proteolytic enzymes not present in broths obtained by cultivating Bacillus lentus DSM 5483. Specifically, fermentation broths obtained by fermentation of the different ATCC 53926 alkaline protease-BLAP constructs in the ATCC 53926 production strain produce the BLAP protease and at least one other proteolytic enzyme produced by the ATCC 53926 strain. Preferably, the BLAP enzyme is obtained as a composition comprising the BLAP enzyme which is a mature alkaline proteolytic enzyme from Bacillus lentus DSM 5483 having the amino acid sequence from about amino acid residue 112 to about amino acid residue 380 substantially as shown in FIG. 1 and at least one other proteolytic enzyme from Bacillus licheniformis ATCC 53926.

The proteases produced by cultivating the ATCC 53926 strain containing the various recombinant plasmids are particularly useful in detergent formulations. They can be formulated with surfactants in accordance with methods known in the art of formulating detergent and cleaning compositions especially laundry detergent compositions. A surfactant is any substance which reduces the surface free energy of water including soaps, nonionic surfactants, anionic surfactants, and cationic surfactants. In the case of laundry detergent formulations, the enzymes can be combined with such suitable surfactants as linear alkyl benzene sulfonates, ethoxylated linear alcohols, ethoxylated alkyl sulfate, or sulfated linear alcohol. The formulation can also contain builders, fluorescent brighteners, bleach, and other components normally used in the art.

DEPOSIT OF MICROORGANISMS

Living cultures of ATCC 53926 and plasmid pCB58C in ATCC 53926, assigned the ATCC Designation 68032, have been accepted for Deposit under the Budapest Treaty on the International Recognition of the Deposit of Microorganisms for the purposes of patent procedure by the American Type Culture Collection, 12301 Parklawn Drive, Rockville, Md. 20852. A living culture of B. lentus DSM 5483 has been accepted for deposit in Deutsche Sammlung yon Mikroorganismen (DSM), Grisebachstr. 8, 3400 Göttingen, Federal Republic of Germany, under the Budapest Treaty on the International Recognition of the Deposit of Microorganisms for the purposes of patent procedure.

The following examples will serve to illustrate but not to limit the invention.

EXAMPLE 1

Construction of a B. lentus DSM 5483 Gene Bank

A. Using the Cosmid Cloning Vector pCP13

The cosmid cloning vector pCP13 was chosen to construct a genomic library from B. lentus DSM 5483 DNA. This broad host range vector derived from the plasmid pLAFR1 (Friedman et. al. Gene(1982) 18, 289) was obtained from F. Ausubel, Department of Molecular Biology, Massachusetts General Hospital, Boston, Mass. Plasmid pCP13 is 23 kb in size and encodes both tetracycline ($Tc^R$) and kanamycin ($Km^R$) resistance, contains multiple unique endonuclease restriction sites, and is mobilizable but not self-transmissible. Cloning into the BamHI site on pCP13 leads to insertional inactivation of the Km resistance determinant, allowing recombinants to be identified by their $Tc^R,Km^S$ phenotype. The vector also contains the lambda cos sites which allows concatemeric forms of the cosmid to be packaged into lambda phage particles using commercially available packaging systems. Inserts in the size range of 12 to 30 kb can be cloned into pCP13, making this cloning vector very attractive for the construction of gene banks. Purified pCP13 DNA (20 μg) was digested with BamHI (3 units (U)/μg) and subsequently dephosphorylated to prevent recircularization. Purified chromosomal DNA (410 μg) from B. lentus strain DSM 5483 was partially digested with BclI (0.0625U/μg DNA) at 50° C. for 60 minutes, and then ligated to the BamHI digested pCP13 DNA. The ligation reaction contained 150 μg/ml pCP13 vector, and 50 μg/ml DSM 5483 chromosomal DNA in a final volume of 30 μl. Ligations were held for 9 hours at 14° C. The ligation mixtures containing concatemeric pCP13-B. lentus genomic DNA fragments were packaged into lambda phage heads using the Packagene Lambda DNA packaging System purchased from Promega, Madison, Wis. The recombinant cosmid molecules packaged into phage particles were used to infect E. coli HB101. E. coli HB101 was grown overnight at 30° C. in a rotary shaker at 175 rpm in 10 ml of Tryptone Broth or TB (per/liter (1), 10 g tryptone, 5 g NaCl, 2 g maltose and 2.46 g $Mg_2SO_4$, sterilized by autoclaving). The cells were pelleted and resuspended in 10 mM $Mg_2SO_4$. Packaging mixture and cells (50 μl and 100 μl respectively) were mixed together and incubated at 37° C. for 20 minutes. Then 1 ml of Luria Broth (per/l, 10 g Bactotryptone, 10 g NaCl, 5 g Yeast extract) was added, and the tubes incubated at 37° C. for 60 minutes in New Brunswick G24 rotary shaker at 150 rpm. The infected HB101 cells were pelleted by centrifugation (13,000 ×g) for 5 min at room temperature, resuspended in Luria Broth, and plated onto Luria agar containing 15 g/ml Tc.

Fourteen hundred $Tc^R$ $Km^S$ HB101 recombinant clones were obtained. To determine the average insert size, plasmid DNA from 14 randomly selected potential clones was isolated, digested with EcoRI, and analyzed by agarose gel electrophoresis. Eleven of the fourteen clones contained inserts with an average insert size of 25.9 kb (range 21.7 to 32.7 kb). Based on this large average insert size, and the assumption that the B. lentus genome is approximately the same size as the E. coli genome, theoretical calculations predicted a 99% probability of detecting the Savinase-like gene by screening 768 cosmid clones.

B. Using the Phage Cloning Vectors EMBL3 and EMBL4

Another method of cloning large pieces of genomic DNA (>10 kb), is to use bacteriophage lambda cloning vectors. These insertion vectors can accept between 9 kb and 23 kb of heterologous DNA. The heterologous DNA and the lambda DNA are necessary to package the recombinant DNA into phage heads which can then be propagated in an *E. coli* host. The EMBL3 and EMBL4 phage vectors were purchased from Stratagene in La Jolla, Calif. These cloning vectors have been constructed with a polylinker region flanking the internal stuffer DNA which is not needed for replication. When the lambda DNA is restricted with the appropriate enzyme, the remaining two DNA fragments called the left and the right arms needed for replication, can be ligated to heterologous DNA. In order for the recombinant DNA to be efficiently packaged into the phage heads, the ligations must be performed at high DNA concentrations to favor the formation of concatamers, and the heterologous insert must be between 9 kb and 23 kb in size. This latter requirement is based on the observation that the length of the DNA which can be packaged is between 70% and 105% of the size of the wild-type lambda genome. Further, both EMBL systems take advantage of spi selection (sensitive to bacteriophage P2 inhibition). EMBL arms ligated to the stuffer fragment and packaged into phage heads cannot grow on a host strain containing a P2 lysogen. In this system, it is unlikely that stuffer fragment and EMBL arms do religate. If this occurs, these phage will not replicate when plated on the appropriate *E. coli* host.

In order to prepare genomic libraries of DSM 5483 DNA in either the EMBL3 or EMBL4 vectors, DSM 5483 DNA was partially digested with either EcoRI or BclI (the 5' sticky end produced by BclI is complementary to the ends of the vector cut with BamHI). In each case, the genomic DNA was digested with less than 1 unit of enzyme per microgram of DNA for 60 minutes. Optimal packaging efficiencies are obtained with lambda DNA's that are concatemeric. Therefore, the ligation reactions were set to achieve DNA concentrations of 200 $\mu$g/ml, which favors concatemer formation. In a standard 5 $\mu$l ligation reaction, 1 $\mu$g of vector arms was mixed with 200 to 400 ng of genomic DNA. Ligation for 1 hour at room temperature was followed by an overnight incubation at 4° C. Concatemeric DNA from the ligation reactions was packaged into phage heads using GigaPack Plus in vitro packaging extract purchased from Stratagene (La Jolla, Calif.), and the protocol provided with the extracts. After packaging, 0.5 ml of phage dilution buffer was added to the packaging reactions (per liter, 5.0 g NaCl, 2 g MgSO$_4$.7H$_2$O, 50 ml 1 M Tris HCl pH 7.5 and 5 ml 2% gelatin) and 20 $\mu$l of chloroform. The packaging reactions were titered, and amplified according to the protocols provided by Stratagene. From each phage library $5 \times 10^5$ recombinant phage were obtained. When a similar experiment was performed with a test insert provided with the commercial cloning kit, $3 \times 10^6$ recombinant phage were obtained. Less than 5% of the plaques generated by the control insert were due to background phage. Recombinant phage had an average insert size of 12–14 kb with about 70% of the phage actually showing inserts. The phage libraries were amplified to a titer of $10^8$ phage/ml and stored over chloroform at 4° C. Other stocks were prepared for longer term storage at −70° C.

To characterize the EMBL libraries and to find the Savinase-like gene, the following approach was undertaken. Groups of plaques were isolated from either the EMBL3 or the EMBL4 libraries, and their DNA was isolated by a phage minipreparation procedure (Maniatis et. al., (1982), A Laboratory Manual, Cold Spring Harbor Laboratories, Cold Spring Harbor, N.Y.). The insert genomic DNA present in the EMBL3 and EMBL4 libraries was digested with either SalI or EcoRI, respectively, and after agarose gel electrophoresis the DNA fragments were transferred to Gene Screen Plus. Total DSM 5483 genomic DNA was nick translated and used as a hybridization probe to verify that the inserts present in the EMBL libraries were really DSM 5483 DNA. As expected, the cloned inserts hybridized with the labelled DSM 5483 DNA. In a second experiment, genomic DSM 5483 DNA was cut with either EcoRI or BclI, electrophoresed in an agarose gel, and then transferred to Gene Screen. DNA isolated from groups of recombinant phage from either the EMBL3 or EMBL4 libraries was nick translated and used as a hybridization probe. As expected, hybridization to DSM 5483 genomic DNA occurred while little or no hybridization was detected to DNA from other Bacillus species. These results verified the formation of gene libraries of *B. lentus* DSM 5483 chromosomal DNA using the lambda EMBL cloning vectors.

EXAMPLE 2

Construction of DNA Probes Specific for the Savinase-like Protease Gene Present in *B. lentus* DSM 5483

A. Oligonucleotide Probes

The gene bank of DSM 5483 chromosomal DNA constructed in *E. coli* with the cosmid pCP13 was screened using oligonucleotide probes. A series of probes of varying degeneracy were synthesized using a Biosearch DNA synthesizer. The sequence of these oligonucleotides was deduced from amino acid sequence data obtained from the N-terminus of the Savinase protease and from the C-terminal fragment of Savinase derived by cyanogen bromide cleavage. The sequence and location of these probes in relation to the Savinase protease are depicted in FIGS. 24 and 25. The NO2 and NO4 series of probes were both designed from N-terminal amino acid sequence data. The NO2 series was 23 bases in length with 14 bases of homology and contained 16 fold degeneracy, while the NO4 series were 17 bases in length with 48 fold degeneracy. The NO4.1–4 series of probes was designed using the most probable codon usage for *B. subtilis*. The CO3 series of oligonucleotides were all 17 bases in length and had a 32 fold degeneracy. These latter probes were designed from amino acid sequence derived from the C-terminal cyanogen bromide fragment of Savinase. These probes were purified, radioactively labeled, and hybridized to chromosomal DNA from DSM 5483 which had been restricted, electrophoresed on agarose gels, and blotted onto nitrocellulose using the procedure of Southern. The restriction enzymes used included EcoRI, HindIII, Taxi, Sau3A, SstI, XbaI, and XhoI. The strongest hybridization signals were obtained with oligonucleotides NO2.2, NO4.2, and CO3.3 (FIG. 25). The latter three labeled oligonucleotides were used to screen Southern blots of restricted chromosomal DNA's from *E. coli*

HB101, B. subtilis DB104, B. licheniformis, and the B. lentus strain, and were found to hybridize only to DNA fragments from the B. lentus strain. This result confirmed that these three oligonucleotides were specific for DNA encoding the Savinase-like protease.

B. Amplification of a Portion of the Alkaline Protease Gene Sequence

Although three of the oligonucleotide probes described above were specific for DSM 5483 chromosomal DNA an additional approach was pursued in order to isolate a larger, double stranded DNA probe specific for the Savinase-like alkaline protease. The N-terminal and internal oligonucleotides described above were utilized as primers in the PCR to amplify that region of DSM 5483 chromosomal DNA extending from the N-terminus to amino acid residue 222 of the mature alkaline protease (FIG. 24). The amino acid sequence obtained from the C-terminal cyanogen bromide fragment from Savinase had homology with the amino acid sequence around the active site region of other serine proteases. If the distance from the N-terminus of Savinase to the active site region was similar to other serine proteases, then the expected size of the amplified fragment would be approximately 650 bp.

The PCR was carried out using a commercial GeneAmp kit purchased from Perkin-Elmer Cetus Instruments. In the PCR, the DNA segment to be amplified may range from a few hundred bp to more than 5 kb in length, and is contained on either a plasmid or on a chromosomal DNA template. Amplification requires the synthesis of two oligonucleotide primers, approximately 15 to 25 bases in length, designed to have homology to opposite DNA strands at either end of the DNA segment. Since DNA synthesis occurs in a 5' to 3' direction, each primer is designed to mimic the corresponding 5' to 3' strand. In the initial experiment, 16 different PCR's were performed using all possible combinations of probe series CO3 with NO2, and DSM 5483 chromosomal DNA as template. The concentration of template and primers was as prescribed in the kit. The PCRs were initiated by mixing template, excess primers, dNTP's, heat stable DNA polymerase, and reaction buffer in eppendorf tubes which were cycled for set periods of time at 94° C., 37° C., and 72° C. In each cycle, the double stranded DNA template was denatured by heating at 94° C., then cooled to 37° C. to allow for annealing of the primers to the appropriate DNA sequences on the single stranded template. The tubes were then shifted to 72° C., where complementary DNA strands were synthesized through elongation of the annealed primers by a heat stable DNA polymerase (Taq polymerase). This process was repeated 25 times, with the amount of amplified DNA doubling after each cycle. One of the PCR (oligonucleotide pair NO2.2 and CO3.3) resulted in the amplification of a single DNA fragment approximately 650 bp in length. Approximately 3 μg of the 650 bp fragment was generated by the PCR, representing about a $5 \times 10^4$ fold amplification. The PCR was repeated using all combinations of the NO4 and CO3 series of probes. Based on the previous result, the combination of NO4.2 and CO3.3 would be expected to produce the amplified 650 bp fragment, and in fact this was the case.

EXAMPLE 3

Identification of Cosmid Clones Carrying the Savinase-like Alkaline Protease Gene From B. lentus To screen for the Savinase-like gene, the 1400 $Tc^R$ $Km^S$HB101 clones were divided into 13 pools of 100–150 clones each. Plasmid DNA from each pool, and from a culture containing the entire gene bank was purified and digested with EcoRI. Restriction fragments were separated by agarose gel electrophoresis and transferred to Gene Screen Plus hybridization membrane (DuPont, Wilmington, Del.) by the methods provided by the manufacturer. In order to detect the Savinase-like gene within the cosmid bank, oligonucleotide probes were synthesized. The predicted sequence of the probes was based on previously acquired amino acid sequence data for the Savinase protease. These probes also served as primers for the synthesis of a 650 bp portion of the BLAP gene using the PCR (described above). The 650 bp PCR fragment was labelled with $^{32}$P in a nick translation reaction (protocol obtained from NEN, Wilmington, Del.) and used as a hybridization probe. This fragment was shown to contain an internal EcoRI site. Therefore, two bands of hybridization would be detected when a complete B. lentus Savinase-like protease gene was present within a cosmid pool digested by EcoRI. When cosmid DNA isolated from the total gene bank of DSM 5483 DNA was digested with EcoRI, two fragments of 6.35 and 2.64 kb were found to hybridize with the labeled 650 bp PCR probe. In six of the recombinant cosmid pools (#3,#4,#8,#11,#12 and #13), these same bands of hybridization were detected, indicating that the Savinase-like gene was present in at least one cosmid clone contained within each of these six pools. Pool #13, which possessed 150 E. coli transformants, was subdivided into 12 subpools of 12 or 13 transformants each. Plasmid DNA from each subpool was isolated, digested with EcoRI, and the DNA fragments separated by gel electrophoresis. After transfer to a Gene Screen Plus membrane, the filter was hybridized to the labeled 650 bp PCR fragment. Two subpools (#7 and #9) were found to contain the same bands of hybridization as detected initially in Pool #13. Plasmid DNA was isolated from each individual transformant in subpools #7 and #9 and the plasmid DNA's were digested with either EcoRI or HindIII in separate reactions. After agarose gel electrophoresis and transfer to Gene Screen Plus, the hybridization procedure was repeated. Cosmid DNA from subpool #9 clone #5 exhibited the same pattern of hybridization expected of a clone which contained the Savinase-like protease gene. When cosmid DNA from clone #5 and DSM 5483 chromosomal DNA were digested with HindIII and probed with the 650 bp PCR fragment, the same band of hybridization was detected for both. A fragment size of 3.4 kb was calculated from the location of the hybridization band in relation to known molecular weight standards. The cosmid from subpool #9 clone #5 was designated pHSH44.

A large scale preparation of the cosmid pHSH44 was prepared by CsCl- ethidium bromide gradient centrifugation, and after dialysis, restricted with HindIII. The HindIII fragments were separated by agarose gel electrophoresis, and the 3.4 kb HindIII fragment which hybridized with the 650 bp PCR fragment was purified, and subcloned into the commonly used E. coli vectors pUC19 and pBR322 for restriction analysis and further subcloning into Bacillus vectors.

EXAMPLE 4

Genetic Characterization of the *B. lentus* Alkaline Protease Gene A. Subcloning and Characterization of a Restriction Fragment Carrying the *B. lentus* Alkaline Protease Gene After purification, the 650 bp fragment was labeled by nick translation and used to probe gene banks of DSM 5483 DNA constructed using the cosmid pCP13 and EMBL lambda vectors. In both cases, using very stringent hybridization conditions positive clones were identified. From hybridization data, several cosmid clones carrying DNA with homology to the 650 bp PCR fragment and selective oligonucleotide probes were identified. Plasmid DNA of one of these cosmids, pHSH44, was purified and characterized by restriction analysis. Results from Southern blots indicated that a DSM 5483 HindIII fragment of approximately 3 to 5 kb hybridized to radioactive probes prepared from the 650 bp PCR fragment. Cosmid pHSH44 carried three HindIII restriction fragments of 3.4 kb, 4.0 kb, and 4.8 kb. Initially, all of these fragments were purified by agarose gel electrophoresis and cloned into both pUC19 and pBR322. The ligation reaction in all cases contained 100 ng of dephosphorylated vector DNA and approximately 1,000 ng of the corresponding HindIII fragment in a volume of 20 μl. These ligation mixtures were transformed into competent cells of either *E. coli* DH5 (for pUC19), or *E. coli* HB101 (for pBR322). Ampicillin resistant transformants were selected and screened for the correct plasmid constructs. All of the HindIII fragments were cloned into both vectors. The correct constructs in pUC19 and pBR322 were designated pMG102.2, and pMG105.9, respectively. The results from hybridization and restriction analysis identified the 3.4 kb HindIII fragment (present in plasmids pMG102.2 and pMG105.9) as having homology to the 650 bp PCR fragment. Plasmid pMG102.2 was purified, and characterized by restriction analysis with 26 different enzymes. In order to obtain the complete nucleotide sequence of the 3.4 kb HindIII fragment, it was necessary to subclone portions of the fragment into the pTZ sequencing vectors. All subclones were made using DNA fragments of pMG102.2 purified from low melting temperature agarose after gel electrophoresis. The excised DNA fragments were ligated to vector DNA which had been restricted at the appropriate sites, and transformed into *E. coli* DH5 cells. Ampicillin resistant transformants were selected and the correct clones identified by restriction analysis. Plasmid DNA's from the correct constructs were purified from the DH5 strain and transformed into *E. coli* NM522 to provided the single stranded templates necessary for DNA sequencing.

B. Sequencing of the 3.4 kb HindIII Fragment Containing the Alkaline Protease Gene of *B. lentus*

The 650 bp PCR fragment was also cloned into *E. coli* plasmid pUC19. The PCR fragment was blunt-end ligated to pUC19 previously digested with SmaI, and transformed into *E. coli* DH5 purchased from Bethesda Research Labs (BRL), using the procedure provided by BRL. Transformants were selected on X-gal plates containing 50 g/ml ampicillin (Maniatis, et al., ibid). Cloning of the 650 bp fragment into the SmaI site would be expected to disrupt lacZ complementation, and therefore produce white colonies on the X-gal plates. Approximately 200 of 10,000 colonies on the X-gal plates were white. Plasmid DNA was prepared from 12 of the 200 transformants and analyzed for the presence of the 650 bp fragment. Seven of the 12 had the PCR fragment cloned into pUC19 in the same orientation. This plasmid was designated pMG100.13. For DNA sequencing, the 650 bp fragment was removed from pMG100.13 by double digestion with BamHI and KpnI. Recognition sites for these enzymes are contained in the polylinker sequence originally from pUC19 but are not found within the DNA sequence of the 650 bp PCR fragment. The BamHI/KpnI PCR fragment was ligated with the commercial (Pharmacia) sequencing vectors pTZ18R and pTZ19R, digested with the same enzymes, and transformed into *E. coli*. Transformants containing the correct constructs were identified by isolation of plasmid DNA and restriction analysis. The two new constructs represented both orientations of the PCR fragment in relation to a sequencing primer site located on the pTZ vectors. DNA sequencing was performed using a dideoxy procedure and a commercially available sequencing primer from the M-13 system. The initial sequencing data consisted of approximately 220 bases for each strand, beginning at either end and extending internal into the 650 bp PCR fragment. This initial sequence confirmed that: the 650 bp PCR fragment had been cloned into the SmaI site of pUC19 as a blunt end fragment; the DNA sequence immediately following the SmaI site in the pTZ18 clone is consistent with the NO2.2 primer; the 17 bp of DNA sequence immediately following the SmaI site in the pTZ19 clone (opposite orientation to pTZ18) is in agreement with the CO3.3 primer; and the amino acid sequences deduced from the DNA sequences both within and extending out from the NO2.2 and CO3.3 primer regions were in agreement with the N-terminal and internal amino acid sequences determined from Savinase. Based on the above results, it can be concluded that the 650 bp PCR fragment amplified from *B. lentus* DSM 5483 DNA represents a portion of a gene encoding an alkaline protease, beginning just after the N-terminus of the mature protease and continuing into the protein coding region. To complete the sequencing of the 650 bp PCR fragment, two approaches were pursued. First, the pTZ19R vector carrying the 650 bp PCR fragment was digested with EcoRI to remove a portion of the PCR fragment, religated, and transformed into *E. coli*. Preliminary restriction analysis of the PCR fragment had revealed an internal EcoRI site, with a second EcoRI site present in the polylinker region of the vector. The correct subclone isolated from this experiment contained the EcoRI site adjacent to the priming site for DNA sequencing, allowing the determination of additional internal DNA sequence of the PCR fragment. At the same time, the small EcoRI fragment removed from the pTZ19R PCR construct was cloned in the opposite orientation into pTZ18R allowing the DNA sequence in the opposite direction from the EcoRI site to be determined.

C. Determining the Transcriptional Start Site for the *B. lentus* 5483 Alkaline Protease Gene A necessary step in the genetic manipulation of the cloned BLAP gene is the determination of the start site of transcription. A primer extension protocol was used to identify this site (Arnosti and Chamberlain (1989), PNAS(U.S.A.), 86, 830). In this procedure, a primer (20 to 30 bases in length) was synthesized which had homology to a sequence on the template DNA positioned 200 to 300 bp 3' to the suspected start of transcription. The primer was hybridized with the messenger RNA transcript under stringent conditions, and then the primer was elongated using the enzyme reverse transcriptase. The size of the reverse transcript was measured in a denaturing polyacrylamide gel. The elongated primer was also sequenced so that the exact base of transcription initiation could be read off of the sequencing gel. Total RNA was isolated as described by Arnosti and Chamberlin (ibid) from DSM 5483 or from the B. subtilis strain DB104 containing plasmid pJW5. Plasmid pJW5 was formed by cloning the 3.4 kb BLAP HindIII fragment into the HindIII site of plasmid pC194. Lysozyme treatment followed by sonication was used to disrupt Bacillus cells. To purify the RNA from contaminating nucleases, at least 4 to 5 phenol extractions were performed. The size of the BLAP gene transcript was determined by Northern analysis, using the protocol described by Thomas ((1983), Methods in Enzymology 100, 255). In this experiment, total Bacillus RNA was denatured and then analyzed by electrophoresis through an agarose gel containing a denaturing concentration of formaldehyde (BRL Focus 9:3,14). The RNA was then transferred from the gel to a nitrocellulose filter which was then baked at 60° C. for 2 hours. Plasmid pMG109.3 (pUC19+the 3.4 kb HindIII fragment containing the BLAP gene) was nick-translated and used to probe the Northern blot. The transcript produced by the BLAP gene was approximately 1,200 to 1,400 bases in length. Two oligonucleotide primers were designed on the basis of the BLAP nucleotide sequence. These primers were homologous to BLAP sequences between the NcoI and the HpaI sites, and 5' to of the sequence encoding the mature protease peptide. Primer A spans the BLAP nucleotide sequence included in FIG. 2 between bases 2056-2033, and primer B is found between bases 2242-2222. The results of the primer extension experiments using either primer and messenger RNA prepared from either B. lentus DSM 5483, or B. subtilis DB104 carrying plasmid pJW5 was the same. In both cases, the start site of transcription was determined to be an adenine residue at position 1924 in the BLAP sequence. This adenine is located 42 bp upstream of the ATG translation initiation codon at the beginning of the BLAP signal peptide. On the basis of this result, the length of the BLAP message is 1210 bases.

EXAMPLE 5

Construction of Fusions Between the B. licheniformis ATCC 53926 Alkaline Protease Gene and the B. lentus Alkaline Protease Gene (BLAP)

A. Experimental Approach

For large-scale production of BLAP, an expression system was designed which was based on gene fusions comprising parts of the ATCC 53926 alkaline protease gene and parts of the BLAP gene. The native promoter of the BLAP gene proved to be insufficient for the effective production of BLAP in B. subtilis DB104 as well as DSM 5483. It was known from fermentation results that the promoter of the ATCC 53926 alkaline protease gene worked well for the large scale production of Carlsberg-type protease in ATCC 53926. Thus, a fusion of the promoter of the ATCC 53926 alkaline protease gene to the structural gene of BLAP potentially would provide an efficient expression system for protease similar to commercially available serine proteases in ATCC 53926. Genes coding for alkaline proteases such as ATCC 53926 and BLAP typically encode a pre-pro form of the enzyme. They all start with a regulatory region comprised of a promoter, ribosome binding site and initiation codon, which is responsible for the efficient transcription and translation of the corresponding gene. The regulatory region is followed by a DNA sequence coding for the signal peptide. The signal sequence which is required for the secretion of the protease outside the cell is followed by a coding region for pro-peptide and the mature protease. After transcription of the DNA sequence downstream from the promoter, the messenger RNA (mRNA) is translated into the final gene product. The pre-pro-mature protease consists of the signal peptide, the pro peptide and the mature protease. The signal sequence directs the immature protease through the cytoplasmic membrane, where the signal peptide is cleaved off enzymatically by a signal peptidase. The pro sequence seems to be essential for a correct folding and processing of the pro-protease during or after translocation across the cytoplasmic membrane and the cell wall. Amino acid sequence comparison between the BLAP and ATCC 53926 alkaline protease gene revealed 49% homology in the pre region, 38% homology in the pro region and 75% homology in the mature region. Because the interaction between the pre and pro regions necessary to obtain correct secretion and maturation of a protease is not fully understood, two different fusions between portions of the ATCC 53926 alkaline protease gene and portions of the BLAP gene were constructed. The two basic fusions were identified by the restriction enzyme sites used to join different portions of the ATCC 53926 and BLAP genes together.

1. ClaI Fusion

In order to construct the ATCC 53926 alkaline protease-BLAP ClaI gene fusion, an extra ClaI restriction site had to be introduced into the ATCC 53926 alkaline protease gene at position 376 next to the junction of the ATCC 53926 pre and pro sequence (FIGS. 27 and 27a). At basepair 2032 the BLAP gene already contained a naturally occurring ClaI site at the corresponding position. The ClaI site was introduced into the ATCC 53926 alkaline protease gene by using the PCR. Plasmid pGM15 described previously was isolated from NM522, a dam+ E. coli strain and restricted with AvaI, ClaI and MluI yielding four DNA fragments of 4330 bp, 1296 bp, 382 bp and 147 bp. The ClaI sites at positions 1206 and 2032 in the BLAP sequence (FIG. 2) were not restricted due to dam-methylation at overlapping GATC sequences. Restriction with MluI was used in order to generate three DNA fragments out of the 1825 bp AvaI/ClaI fragment and to prevent religation and recloning of these fragments to the 4330 bp AvaI/ClaI fragment. The DNA fragments from the pGM15 AvaI/ClaI/MluI digest were ligated to a DNA fragment containing the ATCC 53926 alkaline protease promoter and pre sequence, which was synthesized using the PCR. This 292 bp fragment was flanked by AvaI and ClaI restriction sites at its 5' and 3' ends, respectively, and was synthesized using plasmid pC51 as template with primers #1 and #3 (FIG. 8). The PCR fragment contained sequence information from the N-terminal part of the ATCC 53926 alkaline protease gene including the ATCC 53926 alkaline protease promoter, and most of the ATCC 53926 pre sequence (from the AvaI site at basepair 84 and extending to the newly formed ClaI site at basepair 376). The above ligation was transformed into *E. coli* NM522, and ampicillin-resistant transformants were selected. Plasmid DNA's were prepared and characterized by restriction analysis. A correct construct was identified and designated pCB10C (FIG. 12). Plasmid pCB10C contained the ATCC 53926 alkaline protease promoter and most of the ATCC 53926 pre sequence fused to the BLAP sequence downstream from the native ClaI site at position 2941. Plasmid pCB10C was used to generate the final ClaI-fusion gene by linearizing it with ClaI and inserting a 909 bp ClaI fragment from the BLAP gene which contained the sequence between the ClaI sites at position 2032, and position 2941. The 909 bp ClaI fragment was generated by hydrolyzing plasmid pMG108.2 (FIG. 26) with ClaI. Plasmid pMG108.2 was isolated from *E. coli* GM33 (dam−) in order to prevent dam methylation at adenine residues in the recognition tetranucleotide GATC. The 909 bp DNA fragment 0 was isolated from a preparative agarose gel and ligated into plasmid pCB10C previously having been restricted with ClaI and dephosphorylated with bacterial alkaline phosphatase. The ligation mix was transformed into *E. coli* NM522. Ampicillin resistant transformants were screened and the correct construct (pCB11C) was identified. A restriction map of pCB11C is given in FIG. 4 and a schematic for its construction is given in FIG. 12. Analysis of the DNA sequence across the fusion of the ATCC 53926 and BLAP genes present in plasmid pCB11C confirmed the expected DNA and amino acid sequences.

2. NcoI Fusion

In order to construct the ATCC 53926-BLAP NcoI gene fusion, an extra NcoI restriction site had to be introduced into the ATCC 53926 alkaline protease gene at position 638 near to the junction of the ATCC 53926 pro and mature sequence (FIGS. 27 and 27a). The BLAP gene contained a naturally occurring NcoI site at position 2311. The NcoI site was introduced into the ATCC 53926 sequence by using the PCR. A 554 bp PCR DNA fragment was synthesized using plasmid pC51 as template, and oligonucleotides #1 and #2 (FIG. 8) as primers. The design of the primers introduced AvaI and NcoI sites at the 5' and 3' ends of the fragment, respectively. The 554 bp fragment contained the sequence information for the ATCC 53926 alkaline protease promoter, pre and pro sequences, and the first four amino acids of the mature ATCC 53926 protease gene. After restriction with AvaI/NcoI the PCR fragment was ligated to the 4958 bp AvaI/NcoI DNA fragment from plasmid pGM15. Plasmid pGM15 (FIG. 3) was restricted with AvaI, NcoI and MluI yielding four DNA fragments of 4958 bp, 668 bp, 382 bp, and 147 bp. MluI was used to generate three fragments out of the 1197 bp AvaI/NcoI fragment to prevent religation of this fragment to the 4958 bp AvaI/NcoI fragment. The ligation mix was transformed into *E. coli* NM522. Ampicillin resistant transformants were screened and the correct construct (pCB1N) (FIG. 5) identified. Analysis of the DNA sequence across the NcoI site of plasmid pCB1N confirmed the expected DNA and amino acid sequence. The NcoI fusion alkaline protease gene contained the entire promoter, pre- and pro sequence of the ATCC 53926 and the entire sequence of the mature BLAP with a single amino acid substitution at amino acid residue 3 of the mature BLAP sequence where a threonine replaced a serine.

EXAMPLE 6

Figure 23:
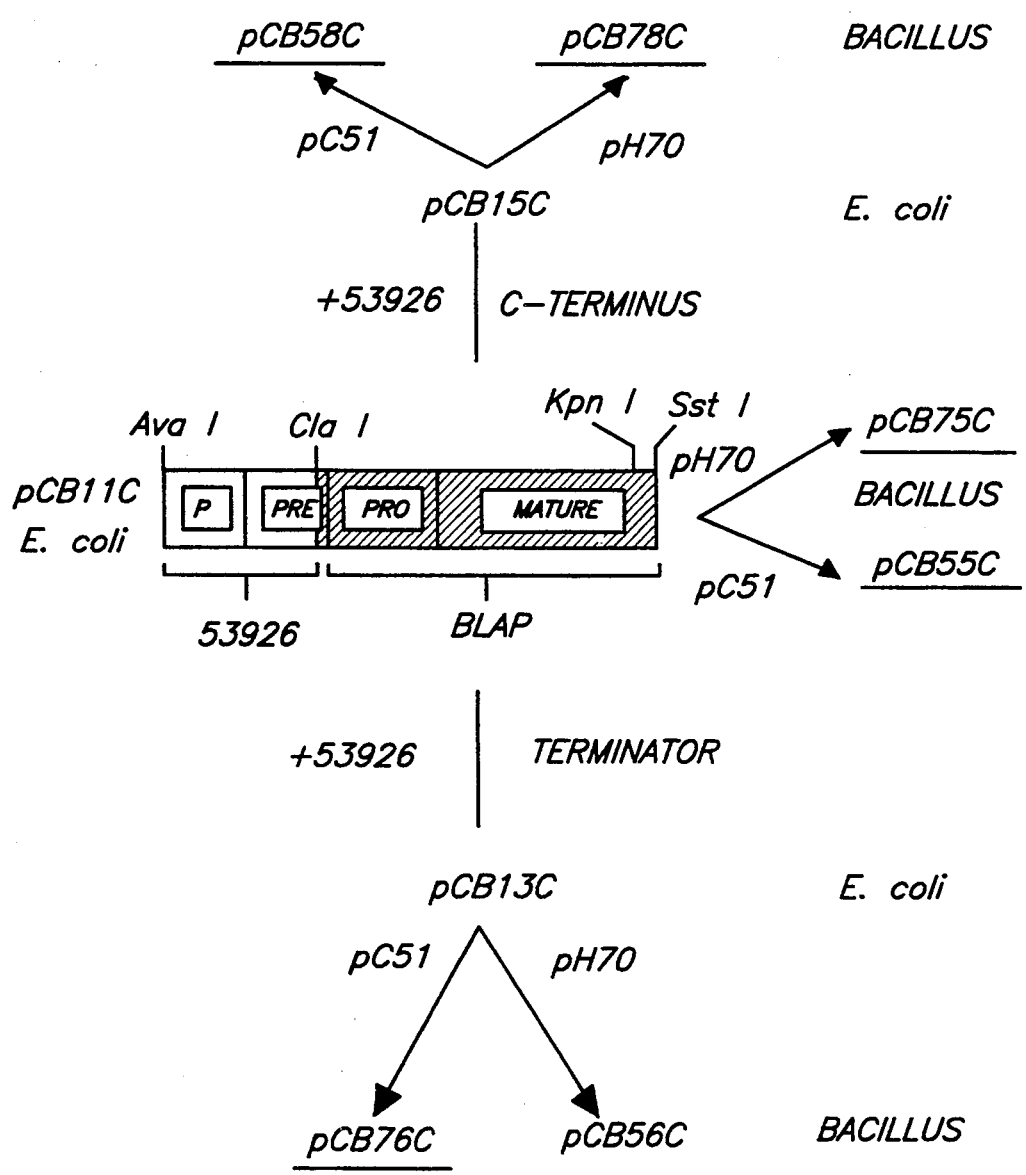
FIG. 23 shows the scheme for construction of the ClaI fusion plasmid constructs in *Escherichia coli* and Bacillus.

Subcloning of the *B. licheniformis* ATCC 53926—BLAP Fusion Gene into Bacillus Vectors and Transformation into the ATCC 53926 Production Strain After the ATCC 53926 alkaline protease-BLAP fusion genes had been cloned into *E. coli* vectors as previously described, they were subcloned into Bacillus vectors and transformed into *B. subtilis* DB104. The ATCC 53926 alkaline protease-BLAP fusion genes were subcloned as AvaI/SstI DNA fragments into pBC16 and pUB110 derivatives by restricting the *E. coli* vectors containing the ATCC 53926 alkaline protease-BLAP fusion genes (pCB1N, pCB11C, pCB2N, pCB13C, pCB4N and pCB15C) with AvaI and SstI, and ligating them to Bacillus plasmids pC51 and pH70 which had been restricted with AvaI, SstI, PstI and SalI. Plasmids pC51 and pH70 were cut with AvaI/SstI to provide the large AvaI/SstI vector fragment containing the necessary origin of replication and an antibiotic resistance gene (tetracycline resistance in pC51, kanamycin resistance in pH70) for selection. Restriction with SalI and PstI was done to hydrolyze the small AvaI/SstI fragment containing the entire ATCC 53926 alkaline protease gene present on pC51, and pH70 into three smaller DNA fragments. This decreased the probability of religating the ATCC 53926 alkaline protease gene into the Bacillus vectors. The initial cloning experiments into Bacillus were done using *B. subtilis* DB104 as recipient. Since DB104 is a reduced protease strain, it provides a direct screen for the presence and expression of the BLAP gene. Using pH70 and pC51 as recipients of the AvaI/SstI fragment from each of the *E. coli*, ATCC 53926 alkaline protease-BLAP fusion plasmids described above resulted in a total of 12 potential Bacillus plasmid constructs. FIG. 23 depicts the six ATCC 53926-BLAP plasmids derived from the three ClaI fusions present in *E. coli* plasmids pCB11C, pCB13C, and pCB15C. Detailed restriction maps of the plasmids that were transformable into the ATCC 53926 production strain, plasmids pCB55C, pCB56C, pCB58C, pCB75C, and pCB78C are shown in FIGS. 13, 14, 15, 16, and 17 respectively. All five of these constructs were transformed into *B. subtilis* DB104 and into the ATCC 53926 production strain. In a similiar fashion, the NcoI ATCC 53926 alkaline protease-BLAP fusions were cloned from pCB1N, pCB2N, and pCB4N into pH70 and pC51. Five of the six plasmids from this cloning (pCB50N, pCB51N, pCB53N, pCB70N, and pCB73N) were transformed into *B. subtilis* DB104, and into the ATCC 53926 production strain. The restriction maps for these constructs are shown in FIGS. 18, 19, 20, 21, and 22 respectively.

EXAMPLE 7

Protocol for Production of *B. lentus* Alkaline Protease (BLAP) by ATCC 53926 Alkaline Protease-BLAP Strains in Shake Flask Cultures To compare derivatives of *B. licheniformis* ATCC 53926 carrying the different ATCC 53926 alkaline protease-BLAP plasmids, a three-stage shake flask procedure was used. In these experiments, the antibiotic tetracycline or kanamycin was always present in the media (described below) to select for the desired plasmid. The first preculture flask was inoculated from a frozen stock vial that had been thawed at room temperature. After 7 hours of incubation at 39° C. and 200 rpm, 1.0% (v/v) of this culture was transferred to a fresh (second) pre-culture flask and the incubation resumed. Between 13 and 15 hours, a 1% transfer was made to duplicate main culture flasks. Culture samples were obtained periodically from the main culture flasks between 27 and 50 hours for determination of protease activity. The shake flask experiments used a complex medium that contained assimilable carbon and nitrogen sources for the microorganism as well as other organic materials and inorganic salts. The major components included hydrolyzed corn starch, sodium caseinate, soy meal, a brewing residue, and corn steep liquor. Small amounts of antifoam, inorganic salts and vitamins B1 and B6 were also present. After distribution to baffled erlenmeyer flasks the medium was sterilized by heating to 121° C. at 15 psi.

EXAMPLE 8

Protocol for Small-Scale Fermentation of ATCC 53926 Derivatives that Produce BLAP The fermentations were carried out in two steps where the organism was first grown up in a shake flask containing a complex medium with antibiotic to select for the endogenous plasmid DNA. After achieving a high cell density, part of the flask culture was transferred to the main fermenter vessel for continued growth and the production of protease. The vessels were Biostat E or ES manufactured by B. Braun, Inc.. All fermentations contained less than 10 liters of culture, and were carried out with BL1 (Biosafety Level One) containment precautions and with good laboratory practices as specified in the National Institutes of Health Guidelines for Research Involving Recombinant DNA Molecules (NIH Guidelines, May 7, 1986).

The shake flask and fermenter media were very similar complex media with an assimilable carbon source, assimilable nitrogen source, organic nutrients and inorganic salts which allowed vigorous growth of the microorganism as well as production of protease. Major medium components included deionized water, corn starch, soy meal, sodium caseinate, a brewing residue, and corn steep liquor. Minor components were $(NH_4)_2HPO_4$ and $Na_2HPO_4$. A commercial antifoam was also present in the fermenter media. The medium was sterilized by heating to 121° C. at 15 psi. The described media in a two-liter baffled flask was inoculated from 1.0 ml of frozen culture-glycerol stock (see stock preparation) that had been thawed at room temperature. Either tetracycline or kanamycin antibiotic was added to the shake flask culture to select for the cells that carried the desired plasmid. The shake flasks were incubated at 39° C. with slow shaking to grow the culture. The fermenter media was eventually inoculated with a 1.5% (v/v) transfer of the shake flask culture. Antibiotic was also present in the fermenter media. The agitation rate and airflow were held at 1,300 rpm and 1 vvm (liters/min.), respectively. In a few experiments, the agitation and airflow rate had to be increased for a brief period during log phase growth to maintain a partial oxygen pressure ($pO_2$) of greater than 20% in the culture.

During cultivation of the production strain, the culture pH and temperature were changed at specified times. In particular, it was found that control of the culture pH had a significant effect on production of protease. The culture pH was controlled at 6.8 from 0–13.5 hours, then controlled at pH 7.5 from 18 to 35 hours. Sterile solutions of KOH and $H_2SO_4$ were added to the media as needed to control pH. From the start of the fermentation the culture temperature was 39° C. The temperature was lowered to 34° C. after 14.5 hours of incubation.

EXAMPLE 9

Assays for the B. lentus Alkaline Protease

For assays of samples from shake flasks or fermentations, the protease was separated from the cells and media debris by centrifugation. The protease in these crude preparations was quantified as described below.

The HPE (Henkel Protease Einheit) method was based on a discontinuous assay of the release of acid-soluble fragments from protease digests of casein. About 50 μl of protease solution was combined with 750 μl of a casein solution prepared by heating Hammarsten casein in tripolyphosphate-tris buffer solution at pH 8.5. After 15 minutes of incubation in a 2.2 ml eppendorf tube at 50° C., 600 μl of 0.44 M trichloroacetic acid solution was added. The mixture was chilled on ice for 15 minutes before removing the precipitate by centrifugation. Acid-soluble peptides were measured in a spectrophotometer at 290 nm. Two HPE units were defined as being equal to an absorbance change of 0.500 OD at 290 nm.

The EPE (Esterolytic Protease Einheit) method was useful primarily for detection of activity from the ATCC 53926 production strain. The kinetic assay was started by mixing 100 μl of a sample or known standard of a commercial protease (Maxatase, Novo A/S) into an acetone buffer containing CBZ-valine-p-nitrophenyl ester. The rate at which p-nitrophenol was released by esterolytic cleavage of the CBZ ester was monitored spectrophotometrically at $A_{340}$ and determined by linear regression analysis. Units of EPE activity for a sample were determined by comparison of the reaction rate of the sample to that of the Maxatase standard.

EXAMPLE 10

Distinguishing between BLAP and B. licheniformis ATCC 53926 Protease by Gel Electrophoresis The B. lentus alkaline protease produced by the ATCC 53926 alkaline protease-BLAP fusion strains could be distinguished from ATCC 53926's native extracellular proteolytic enzymes by electrophoresis in homogeneous, non-denaturing ("native") 12.5% polyacrylamide (PA) gels with pH 6.0 buffer. Crude samples obtained by centrifugation of the fermenter broth were resolved by this method on the PhastSystem apparatus manufactured by Pharmacia, Inc.. The protein species were visualized by staining the PA gel in Coomassie Blue.

EXAMPLE 11

Preparation of B. licheniformis ATCC 53926

Cell material from agar slants containing strain B. licheniformis DSM641 was transferred by a loop and suspended in 5 ml of medium A (Medium A: Nährbouillion from Merck prepared according to the manufacturer's directions). After intensive agitation in a Vibrox the suspension was agitated at 30° C. in a circular shaker (150 RPM, amplitude of 2.5 cm; 24 hr). After 24 hours, 1 ml of the suspension (Optical Density=1 at 640 nm) was incubated in 100 ml of medium A in a 500 ml Erlenmeyer shake flask for an additional 24 hours. Then it was centrifuged off at 6,500 rpm. The centrifugate was rinsed twice with an isotonic NaCl solution and placed in enough salt water to give a cell count of approx. $10^9$/ml.

About 8 ml of the suspension were transferred to a 9 cm diameter Petri dish for U.V. radiation (5–60 minutes) at a distance of 27 cm from the U.V. lamp (Schutt/Göttingen) while agitating at 100 rpm. The agitation was continued during radiation to prevent settling of the cells. After the desired radiation time, preferably 6 minutes, a dilution series was made and these dilutions were plated on medium-A agar plates with and without antibiotic. From the determination of CFU (Colony Forming Units) before and after mutagenic treatments, with and without antibiotics, the mortality rate can be determined as well as changes in reversion rate which serves as a measurement for mutation formation. In the case of DSM 641, a mortality rate of >95% was considered to be especially desirable.

Using a replica plating technique, the colonies were transferred to Ca-caseinate-agar. The plates were incubated at 39° C. for 72 hours. Then at 24, 48, and 72 hours the formation of clearing zones around the colonies was measured. After measuring the colonies and the clearing zones, the strains were selected which showed a large lysis area as compared with the diameter of the colony. Then individual cultures of these colonies were produced using the standard microbiological procedures (Koch's Agar Plate Procedure, Lindner's Drop Procedure, Multiple Streak Procedure). Shake flask experiments were undertaken with these isolates to determine protease productivity.

EXAMPLE 12

Comparison of Protease Production by DSM641 and ATCC 53926

The strains were incubated in shake flasks with 50 ml of medium B (see footnote 1 to Table III) in a 500 ml Erlenmeyer for 96 hours at 39° C. and 150 RPM (amplitude of 5 cm). The protease activity was determined every 24 hours. The relative protease production is summarized in Table III.

TABLE III

| Strain | Protease activity EPE/ml | | Ratio Rel. to DSM641 | | Average Protease EPE/ml | | Ratio Avg Rel. to DSM641 | |
|---|---|---|---|---|---|---|---|---|
| | $72^3$ | 96 | 72 | 96 | 72 | 96 | 72 | 96 |
| $53926^2$ | 4950 | 6702 | 1.36 | 1.32 | | | | |
| 53926 | 5298 | 6340 | 1.45 | 1.35 | 5120 | 6270 | 1.35 | 1.33 |
| DSM641 | 3950 | 4920 | 1.08 | 1.05 | | | | |
| DSM641 | 3650 | 4690 | 1.00 | 1.00 | 3800 | 4805 | 1.00 | 1.00 |

1. Medium B:
| | |
|---|---|
| KH$_2$PO$_4$ | 2.5 g/l |
| MgSO$_4$ × 7H$_2$O | 1.0 g/l |
| MnSO$_4$ × 2H$_2$O | 0.5 g/l |
| CaCl$_2$ × 2H$_2$O | 0.2 g/l |
| Soy bean meal | 3.0 g/l |
| Casein nach Hammersten | 15.0 g/l |
| Potato starch | 120.0 g/l |
| Amylase | 0.6 g/l |

The potato starch which is suspended in ⅓ of the final volume was enzymatically hydrolyzed. Separately, the casein was dissolved at 75° C. in water (about ⅓ of the total volume) by addition of the KOH solution. These two solutions were combined with the salts and the total volume adjusted with water. The pH was adjusted to 7.2 and then the solution was sterilized.
[2]Duplicate fermentations were performed.
[3]The entries 72 and 96 refer to incubation time in hours.

Table III shows that the strain ATCC 53926 produces about 30% more protease compared to strain DSM641.

Miscellaneous Experimental Operations

1. Preparation of Plasmid DNA

Plasmid preparation (mini-prep. and CsCl/ethidium bromide density gradient purified),agarose and acrylamide gel electrophoresis, buffers (TE- Tris EDTA, TAE- Tris acetate EDTA, TBE- Tris borate EDTA) and media preparation were essentially performed as described by Maniatis, et al., (ibid). Phenol p.a. was purchased from IBI and equilibrated with TE-buffer prior to use. Agarose (SeaKem GTG) and low gelling temperature agarose (SeaPlaque) were purchased from FMC Corp., Rockland, Me.

2. Purification of Restriction Fragments

Restriction fragments were isolated by running the sample on a preparative agarose gel. DNA was visualized by staining with ethidium bromide and the band with the DNA fragment to be recovered cut out with a razor blade. The DNA was electroeluted using an IBI electroeluter, phenolized once and precipitated with ethanol.

3. Polymerase Chain Reaction

The PCR was performed exactly as described by the manufacturer (Cetus Corporation, Emeryville, Calif.). The solution containing the DNA generated by PCR was extracted with phenol, precipitated with ethanol and resuspended in an appropriate buffer for hydrolysis with restriction enzymes. After hydrolysis with the appropriate restriction enzyme, the solution was extracted with phenol and the DNA was precipitated with ethanol. DNA prepared in this manner was suitable for ligation. In this report the expected length of all PCR generated DNA fragments corresponded to the size of the DNA fragments observed after restriction with the appropriate restriction enzymes.

4. Restriction Analysis

Restriction enzymes, T4 DNA Ligase and bacterial alkaline phosphatase were used as described by the manufacturers (NEB, BRL, IBI, Boehringer).

5. Protoplast Transformation

The method of protoplast transfromation originally optimized for B. subtilis was adapted to other Bacillus species (Chang and Cohen (1979) Mol. Gen. Genetics 168, 111). A colony of B. subtilis, B. lentus, or B. licheniformis was inoculated into 30 ml of 416 media (416 media: 2% Bactotryptone, 1% Yeast Extract, 1% NaCl, sterilized by autoclaving) and grown overnight at 37° C. in a New Brunswick G24 tabletop shaker at 225 rpm. The next morning, an appropriate volume of each culture was used to inoculate 40 ml of 416 broth (prewarmed) in a sterile 250 ml Erlenmeyer flask. Incubation at 37° C. was continued with shaking, until an OD$_{650}$ between 0.4 and 0.5 was reached. Then the cells were pelleted in a sterile 35 ml polypropylene Oakridge type tube, 3,000 rpm, 10 min at 4° C. The supernatant was removed by pouring, and the cell pellet gently resuspended in 5 ml of SMMP by inversion. SMMP was always prepared fresh by mixing equal volumes of 2X SMM and 4X PAB (2X SMM contained: 1.0 M Sucrose, 0.04 M Maleic Acid, 0.04 M MgCl$_2$.6H$_2$O, pH6.5 adjusted with 10% NaOH, sterilized by autoclaving: 4X PAB contained: 70 g of Difco Antibiotic Medium #3 dissolved in one liter of deionized water and sterilized by autoclaving). The cell suspension was transferred by pouring into a sterile 16×125 mm round bottom, screw-cap culture tube (Corning #25760). A lysozyme solution, 10 mg/ml in SMMP was prepared fresh, and 200 μl added to the cell suspension. The tubes were placed on the platform of a G24 New Brunswick shaker, and incubated at 37° C. with very gentle shaking (25-30 rpm). Protoplast formation generally took 40-60 minutes for *B. licheniformis,* and 20-40 minutes for *B. lentus* and *B. subtilis.* To determine the degree of protoplasting, a sample of the cell suspension was examined using the phase contrast microscope. Following the lysozyme treatment, 10 ml of SMMP was added to the protoplast suspension and the protoplasts were pelleted by centrifugation at 2,000 rpm for 10 minutes at room temperature. The supernatant was carefully removed before resuspending the protoplast pellet in SMMP (3 ml of SMMP for each 40 ml of initial cell culture). In each transformation reaction, 0.5 ml of protoplasted cells was transferred into a sterile, plastic 16×125 mm round bottom culture tube (Corning #256760), followed by the addition of one to four micrograms of DNA in a volume of 60 μl or less, and 1.5 ml of 40% polyethylene glycol (PEG, Sigma Chemical Company product #P-3640). After gentle mixing of the tubes by inversion they were allowed to sit at room temperature for 3-4 minutes, and then the PEG was diluted by the addition of 5 ml of SMMP+2% BSA (Bovine Serum Albumin). After mixing by inversion, the protoplasts were pelleted by centrifugation at 2,000 rpm for 10 minutes at room temperature, and the supernatant was carefully poured off before resuspending the pellet in 1.0 ml of SMMP+BSA. The cells were then incubated at 37° C. for 90 minutes with shaking (New Brunswick G24 table top shaker, 150 rpm) to allow for expression of plasmid encoded genes, and to partially regenerate cell walls. Selective regeneration medias were prepared with the appropriate antibiotic. The CR5 regeneration medium was used for all Bacillus strains when selecting for transformants containing plasmids encoding $Km^R$ (Puyet et al. (1987) FEMS Microbiology Letters 40, 1). The DM3 regeneration medium was originally used to select all Bacillus strains transformed by plasmids encoding $Tc^R$ (Chang and Cohen (ibid)). However, *B. lentus* protoplasts were discovered to regenerate inefficiently on this succinate based media. Therefore, #451 regeneration medium which used mannitol as an osmotic stabilizer was tested (Bourne and Dancer (1986) J. of Gen. Micro. 132, 251). All of the Bacillus strains were found to regenerate well on the mannitol media, although the level of tetracycline needed for each strain was different. The selective levels of tetracycline for *B. subtilis, B. lentus,* and ATCC 53926 were 65 μg/ml, 15 μg/ml, and 25 μg/ml, respectively. Each transformation reaction was plated onto 5 regeneration plates and incubated 1-2 days at 37° C. Potential transformants were picked onto Luria Agar containing the appropriate antibiotic, and when necessary 1% skim milk to detect protease activity. To check strain identity, Spizizens's minimal salts medium with and without the correct nutritional additives were used.

6. Bacterial Strains

*Escherichia coli* Strains

1. *E. Coli* NM522 is hsd 5, (lac-pro), [F', pro+, lacI$^q$Z M15]. NM522 is restriction minus and modification minus (Pharmacia, Piscataway, N.J.)

2. *E. coli* GM33 (dam3) is dam-methylase minus (Marinus, M. G. and Morris, N. R., (1974) J. Mol. Biol. 85, 309).

3 *E. coli* DH5 is F- 80dlacZ M15 (lacZYA-argF)U169, recA1, endA1, hsdR17($r_k^-$,$m_k^+$), supE44, lambda-, thi-1, gyrA, relA1 (competent frozen cells, BRL, Gaithersburg, Md.).

4. *E. coli* HB101 is F-, hsdS20 ($r_B^-$, $m_B^-$), supE44, ara14, glaK2, lacYi, proA2, rpsL20(str$^R$), xy115, leu, mtl1, lambda-, recA13.

7. Bacillus Strains:

1. *B. subtilis* DB104 has the genotype: his, nprR2, nprE18, and aprA3. This strain was obtained from Dr. Roy Doi at the University of California at Davis through a licensing agreement, and has only been used for research purposes. This strain is deficient in the production of neutral and alkaline protease.

2. *B. licheniformis* ATCC 53926 is an industrial production strain developed by Henkel KGaA, Düsseldorf, West Germany.

3. *B. lentus* DSM 5483 is a natural isolate of a soil sample from West Germany.

8. Cloning Vectors 1. pUC19: pUC19 is a small *E. coli* plasmid (2686 bp) containing parts of pBR322 and M13mp19. It carries a 54 bp multiple cloning site with recognition sites for 13 different restriction endonucleases. It has been constructed by C. Yanisch-Perron et al. ((1985), Gene 33, 103), and can be purchased from New England Biolabs, Inc., Beverly, Mass.

2. pTZ18R: pTZ18R (Mead, D. A. et al. (1986) Protein Engineering, 1, 67) is a multifunctional phage plasmid (phasmid) vector. It contains origins of replication of the *E. coli* vector pBR322 and of the *E. coli* phage f1, allowing single-stranded DNA to be produced. It contains the multiple cloning site of plasmid pUC18. It can be purchased from Pharmacia LKB Biotechnology, Inc., Piscataway, N.J.

3. pTZ19R: pTZ19R is homologous to pTZ18R but contains the multiple cloning site of plasmid pUC19.

4. pCP13: pCP13 is a broad host range cosmid vector derived from plasmid pLAFR1, which has been previously characterized (Friedman, et al., (1982) Gene 18, 289). Plasmid pCP13 is 23 kb in size, and encodes resistance to tetracycline and kanamycin. It contains multiple unique restriction sites suitable for cloning, can be mobilized, but is not self-transmissible.

5. pC50: pC50 is a derivative of the Bacillus plasmid pBC16. It contains a 2 kb DNA fragment encoding the DSM641 protease cloned into the BamHI site of pBC16.

6. pC51: pC51 is a second generation derivative of plasmid pC50. The 1540 bp AvaI/SstI fragment from pC50 which encodes an ATCC 53926 alkaline protease, was first cloned into the *E. coli* plasmid pUC19 between the XmaI and SstI sites to form plasmid pH9. The ATCC 53926 protease gene was then removed from pH9 on an EcoRI/BamHI fragment and cloned into plasmid pBC16 between the EcoRI and BamHI sites to form plasmid pC51.

7. pUB110: pUB110 is a 4548 bp plasmid encoding resistance to kanamycin, which was originally isolated from *Staphylococcus aureus* by R. W. Lacey ((1974) J. Med. Microbiol., 7, 285).

8. pKO110: pKO110 is a derivative of pUB110 in which the 788 bp EcoR1/BamHI fragment has been removed, and replaced by a fragment from pUC19 containing the polylinker region.

9. pBC16: pBC16 has an approximate size of 4250 bp, and encodes resistance to tetracycline. This plasmid was originally isolated from *Bacillus cereus* and transformed into *B. subtilis* (Bernhard, K., et. al., (1978) J. Bacteriol.133:897).

10. pC194: pC194 is a 2910 basepair plasmid encoding resistance to chloramphenicol which was isolated from

*S. aureus* and transformed into *B. subtilis*. (Iordanescu, S., et. al., (1978) Plasmid 1:468) and (Erlich, S. D. (1977), PNAS USA 74:1680).

11. pH70: pH70 is a derivative of plasmid pUB110. The ATCC 53926 alkaline protease gene was removed from plasmid pH9 (see plasmid pC51) on an EcoRI/BamHI DNA fragment and cloned into plasmid pUB110 between the EcoRI and BamHI sites to form plasmid pH70.

What is claimed is:

1. A composition comprising a mature alkaline proteolytic enzyme from *Bacillus lentus* DSM 5483 and at least one other proteolytic enzyme from *Bacillus licheniformis* ATCC 53926, wherein the amino acid residues of said enzyme from *Bacillus lentus* DSM 5483 at positions 208, 210, 212, 213 and 268 are identical with those of FIG. 1 and wherein the remaining amino acid residues of said enzyme share no less than 95% homology therewith, and with at least one other mature protease of Bacillus.

2. A composition comprising a mature alkaline proteolytic enzyme having the amino acid sequence substantially as shown in FIG. 29 and at least one other proteolytic enzyme from *Bacillus licheniformis* ATCC 53926 wherein the amino acid residues of said enzyme substantially similar to that represented in FIG. 29 are identical with those of FIG. 29 at position 3, 97, 99, 102 and 157 and wherein the remaining amino acid residues share no less than 95% homology therewith, and at least one other mature protease of *Bacillus licheniformis* ATCC 53926.

3. A composition of claim 1 further comprising a surfactant.

4. A composition of claim 3 wherein said surfactant is selected from the group consisting of a linear alkyl benzene sulfonate, an ethoxylated linear alcohol, an alkyl ethoxylated sulfate, a sulfated linear alcohol, or combinations thereof.

* * * * *